(12) United States Patent
Tomita et al.

(10) Patent No.: US 12,325,729 B2
(45) Date of Patent: Jun. 10, 2025

(54) MODIFIED CHANNEL RHODOPSIN

(71) Applicant: NATIONAL UNIVERSITY CORPORATION, IWATE UNIVERSITY, Morioka (JP)

(72) Inventors: Hiroshi Tomita, Morioka (JP); Eriko Sugano, Morioka (JP); Kitako Tabata, Morioka (JP); Yoshito Watanabe, Morioka (JP)

(73) Assignee: NATIONAL UNIVERSITY CORPORATION, IWATE UNIVERSITY, Morioka (JP)

( * ) Notice: Subject to any disclaimer, the term of this patent is extended or adjusted under 35 U.S.C. 154(b) by 1078 days.

(21) Appl. No.: 17/277,468

(22) PCT Filed: Sep. 15, 2019

(86) PCT No.: PCT/JP2019/036252
§ 371 (c)(1),
(2) Date: Mar. 18, 2021

(87) PCT Pub. No.: WO2020/059675
PCT Pub. Date: Mar. 26, 2020

(65) Prior Publication Data
US 2021/0347831 A1 Nov. 11, 2021

(30) Foreign Application Priority Data
Sep. 20, 2018 (JP) .................. 2018-176671

(51) Int. Cl.
*A61K 38/17* (2006.01)
*A61K 48/00* (2006.01)
*A61P 27/02* (2006.01)
*C07K 14/405* (2006.01)
*C07K 14/705* (2006.01)
*C07K 14/72* (2006.01)
*C07K 19/00* (2006.01)
*C12N 5/10* (2006.01)
*C12N 15/86* (2006.01)
*A61K 38/00* (2006.01)

(52) U.S. Cl.
CPC ............ *C07K 14/405* (2013.01); *A61K 38/17* (2013.01); *A61K 38/1796* (2013.01); *A61K 48/005* (2013.01); *A61P 27/02* (2018.01); *C07K 14/705* (2013.01); *C07K 14/723* (2013.01); *C07K 19/00* (2013.01); *C12N 5/10* (2013.01); *C12N 15/86* (2013.01); *A61K 38/00* (2013.01)

(58) Field of Classification Search
CPC .............. A61K 38/177; A61K 38/1796; C07K 14/705; C07K 14/723
See application file for complete search history.

(56) References Cited

U.S. PATENT DOCUMENTS

| 8,754,048 B2 * | 6/2014 | Tomita ................. C07K 14/405 514/20.8 |
| 2012/0190629 A1 | 7/2012 | Tomita |
| 2015/0232528 A1 | 8/2015 | Spudich |

FOREIGN PATENT DOCUMENTS

| WO | 2011/019081 A1 | 2/2011 |
| WO | 2015/148974 A2 | 10/2015 |

OTHER PUBLICATIONS

Extended European Search Report for corresponding European Patent Application No. 19861516.3 dated Oct. 28, 2022 (21 sheets).
International Search Report for International Application No. PCT/JP2019/036252 dated Dec. 10, 2019 (2 sheets).
M. Prigge, et al.; "Color-tuned Channelrhodopsins for Multiwavelength Optogenetics"; The Journal of Biological Chemistry, 2012; vol. 287; No. 38; pp. 31804-31812 (9 pages).
S. Hososhima, et al.; "Kinetic Evaluation of Photosensitivity in Bi-Stable Variants of Chimeric Channelrhodopsins"; PLOS One; 2015; pp. 1-14 (14 pages).
H. Wang, et al.; "Molecular Determinants Differentiating Photocurrent Properties of Two Channelrhodopsins from Chlamydomonas"; The Journal of Biological Chemistry; 2009; vol. 284; No. 9; pp. 5685-5696 (12 pages).
O. Sineshchekov, et al.; "Intramolecular Proton Transfer in Channelrhodopsins"; Biophysical Journal; 2013; vol. 104; pp. 807-817 (11 pages).
Supplementary Partial European Search Report for European Patent Application No. 19861516.3 dated Jun. 21, 2022 (19 sheets).
P. Hegemann, et al.; "Channelrhodopsin engineering and exploration of new optogenetic tools"; Nature Methods; 2011; vol. 8; No. 1; pp. 39-42 (4 pages).
J. Lin, et al.; "Characterization of Engineered Channelrhodopsin Variants with Improved Properties and Kinetics"; Biophysical Journal; 2009; vol. 96; No. 5; pp. 1803-1814 (12 pages).

(Continued)

*Primary Examiner* — Jeffrey E. Russel
(74) *Attorney, Agent, or Firm* — Kratz, Quintos & Hanson, LLP

(57) ABSTRACT

An object of the present invention is to provide a modified channel rhodopsin capable of opening and closing an ion channel by irradiation with light at different wavelengths, and/or having high ion permeability (photoreactivity). The solution is to substitute a C-terminal region of a channel rhodopsin obtained by substituting an N-terminal region of a *Volvox carteri*-derived channel rhodopsin by an N-terminal region of a *Chlamydomonas reinhardtii*-derived channel rhodopsin-1, by a C-terminal region of a *Chlamydomonas reinhardtii*-derived channel rhodopsin-2 or a C-terminal region of a *Tetraselmis striata*-derived channel rhodopsin.

8 Claims, 4 Drawing Sheets
Specification includes a Sequence Listing.

(56) References Cited

OTHER PUBLICATIONS

J. Lin, et al.; "ReaChR: a red-shifted variant of channelrhodopsin enables deep transcranial optogenetic excitation"; Nature Neuroscience; 2013; vol. f16; No. 10; pp. 1499-1508 (10 pages).
K. Erbguth, et al.; "Biomodal Activation of Different Neuron Classes with the Spectrally Red-Shifted Channelrhodopsin Chimera C1V1 in Caenorhabditis elegans"; PLOS One; 2012; vol. 7; No. 10; pp. 1-9 (9 pages).

\* cited by examiner

[FIG. 1]
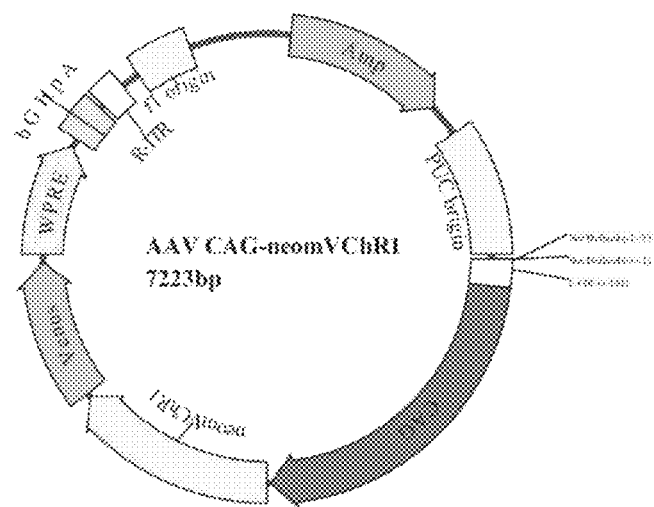

[FIG. 2]
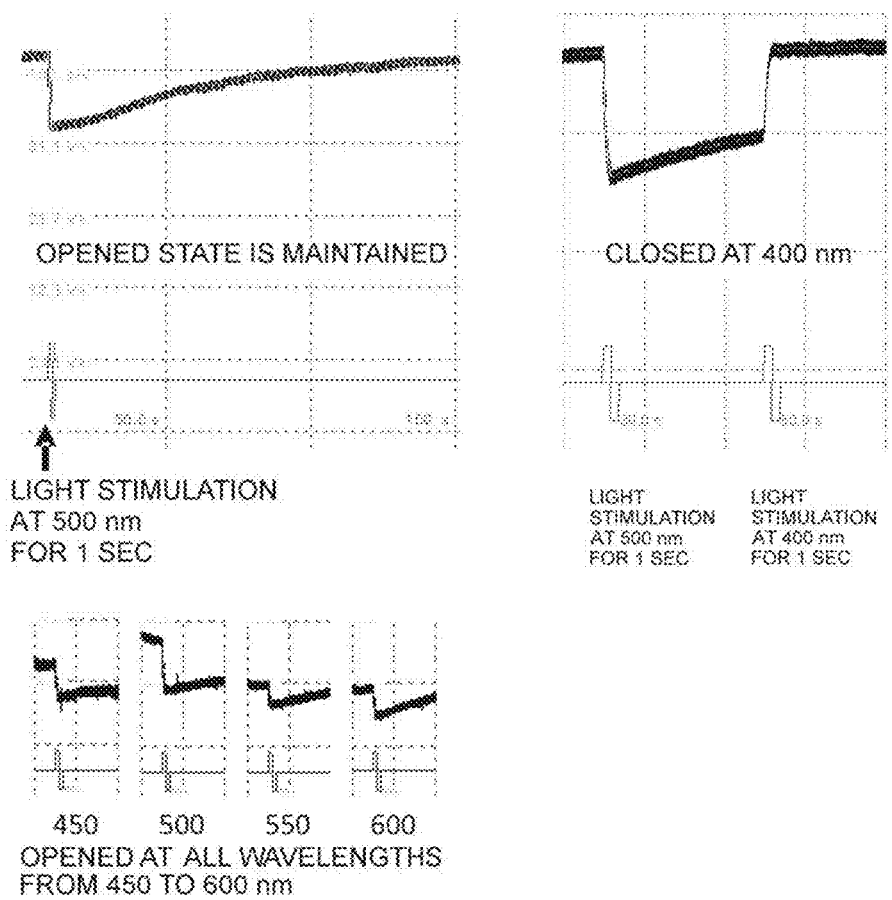
[FIG. 3]
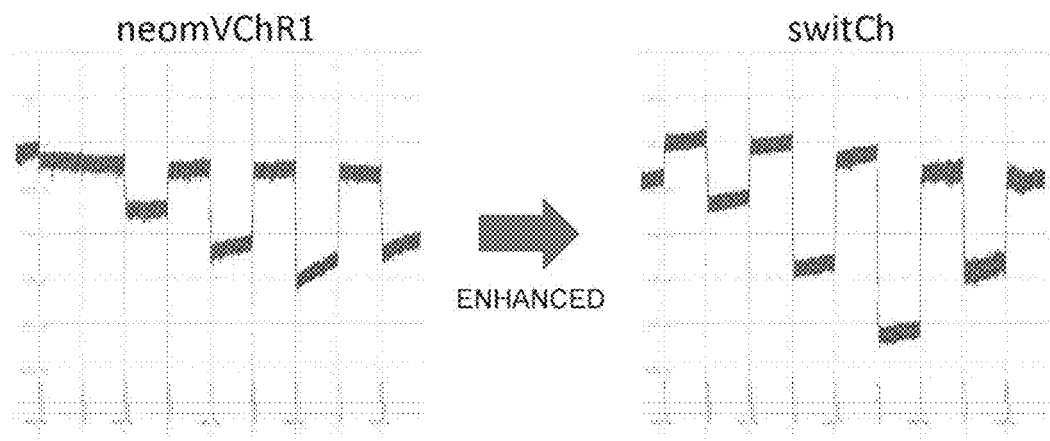

[FIG. 4]
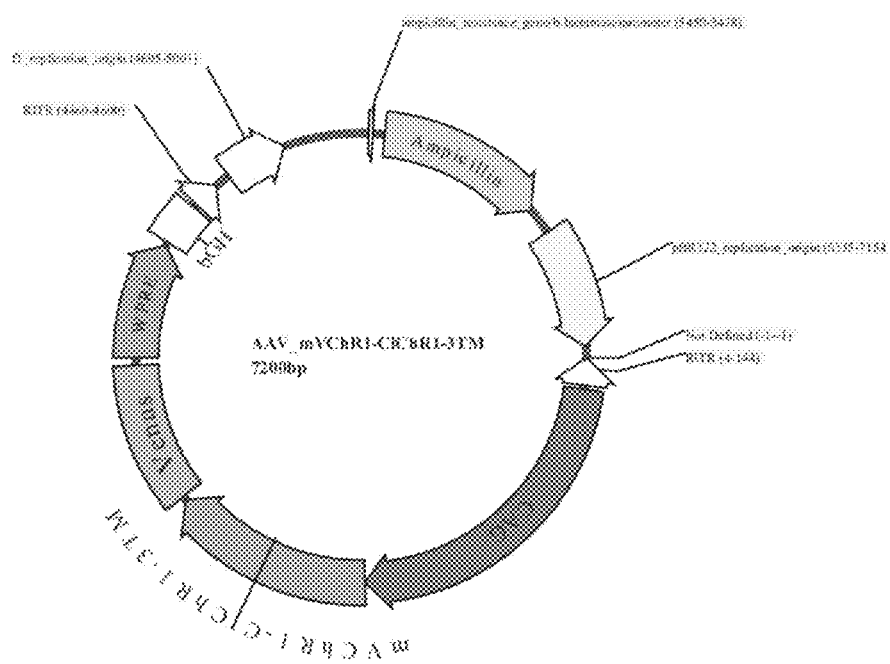
[FIG. 5]
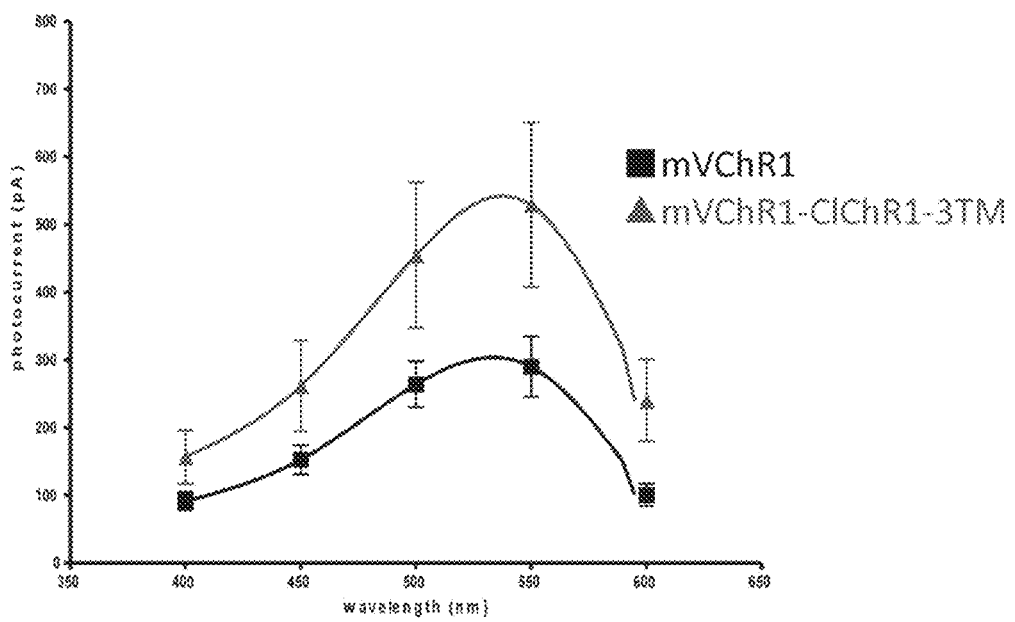

[FIG. 6]
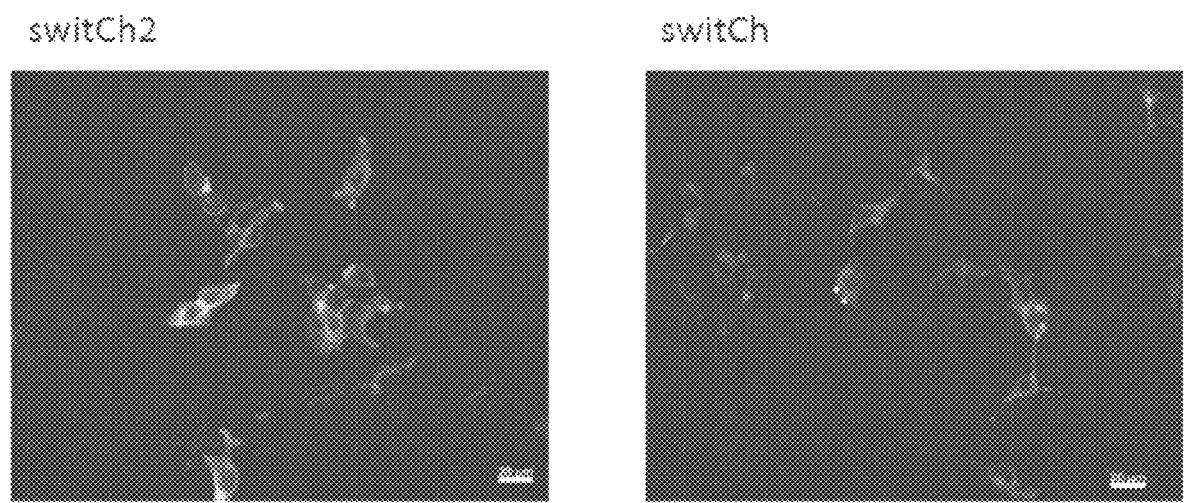
[FIG. 7]
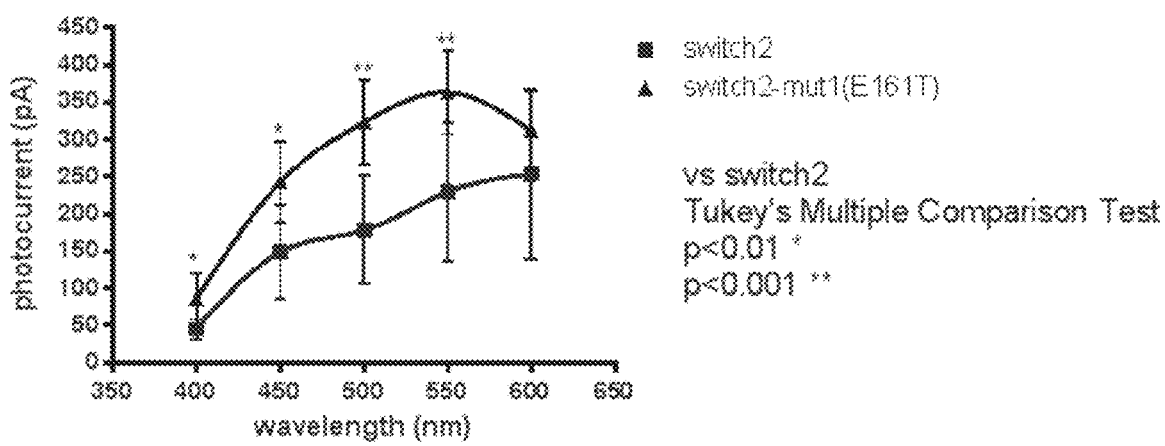

SEQUENCE LISTING

```
<160> NUMBER OF SEQ ID NOS: 16

<210> SEQ ID NO 1
<211> LENGTH: 344
<212> TYPE: PRT
<213> ORGANISM: Artificial Sequence
<220> FEATURE:
<223> OTHER INFORMATION: Fusion protein having Volvox ChR1 and
      N-terminus reagion of Chlamydomonas ChR1

<400> SEQUENCE: 1

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Met Pro Arg Gly Gln Cys Tyr Cys Glu Gly Trp Leu Arg Ser
65                  70                  75                  80

Arg Gly Thr Ser Ile Glu Lys Thr Ile Ala Ile Thr Leu Gln Trp Val
                85                  90                  95

Val Phe Ala Leu Ser Val Ala Cys Leu Gly Trp Tyr Ala Tyr Gln Ala
            100                 105                 110

Trp Arg Ala Thr Cys Gly Trp Glu Glu Val Tyr Val Ala Leu Ile Glu
        115                 120                 125

Met Met Lys Ser Ile Ile Glu Ala Phe His Glu Phe Asp Ser Pro Ala
    130                 135                 140

Thr Leu Trp Leu Ser Ser Gly Asn Gly Val Val Trp Met Arg Tyr Gly
145                 150                 155                 160

Glu Trp Leu Leu Thr Cys Pro Val Leu Leu Ile His Leu Ser Asn Leu
                165                 170                 175

Thr Gly Leu Lys Asp Asp Tyr Ser Lys Arg Thr Met Gly Leu Leu Val
```

```
                180             185             190
Ser Asp Val Gly Cys Ile Val Trp Gly Ala Thr Ser Ala Met Cys Thr
            195                 200             205

Gly Trp Thr Lys Ile Leu Phe Phe Leu Ile Ser Leu Ser Tyr Gly Met
            210             215                 220

Tyr Thr Tyr Phe His Ala Ala Lys Val Tyr Ile Glu Ala Phe His Thr
225                 230                 235                 240

Val Pro Lys Gly Ile Cys Arg Glu Leu Val Arg Val Met Ala Trp Thr
                245                 250                 255

Phe Phe Val Ala Trp Gly Met Phe Pro Val Leu Phe Leu Leu Gly Thr
            260                 265                 270

Glu Gly Phe Gly His Ile Ser Pro Tyr Gly Ser Ala Ile Gly His Ser
            275                 280                 285

Ile Leu Asp Leu Ile Ala Lys Asn Met Trp Gly Val Leu Gly Asn Tyr
            290                 295                 300

Leu Arg Val Lys Ile His Glu His Ile Leu Leu Tyr Gly Asp Ile Arg
305                 310                 315                 320

Lys Lys Gln Lys Ile Thr Ile Ala Gly Gln Glu Met Glu Val Glu Thr
                325                 330                 335

Leu Val Ala Glu Glu Asp Arg
            340

<210> SEQ ID NO 2
<211> LENGTH: 315
<212> TYPE: PRT
<213> ORGANISM: Chlamydomonas reinhardtii

<400> SEQUENCE: 2

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
            115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
            195                 200                 205
```

```
Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
                275                 280                 285

Ile Gly Gly Thr Glu Ile Glu Val Glu Thr Leu Val Glu Asp Glu Ala
290                 295                 300

Glu Ala Gly Ala Val Asn Lys Gly Thr Gly Lys
305                 310                 315

<210> SEQ ID NO 3
<211> LENGTH: 293
<212> TYPE: PRT
<213> ORGANISM: Tetraselmis striata

<400> SEQUENCE: 3

Met Phe Ala Ile Asn Pro Glu Tyr Met Asn Glu Thr Val Leu Leu Asp
1               5                   10                  15

Glu Cys Thr Pro Ile Tyr Leu Asp Ile Gly Pro Leu Trp Glu Gln Val
                20                  25                  30

Val Ala Arg Val Thr Gln Trp Phe Gly Val Ile Leu Ser Leu Val Phe
            35                  40                  45

Leu Ile Tyr Tyr Ile Trp Asn Thr Tyr Lys Ala Thr Cys Gly Trp Glu
50                  55                  60

Glu Leu Tyr Val Cys Thr Val Glu Phe Cys Lys Ile Ile Ile Glu Leu
65                  70                  75                  80

Tyr Phe Glu Tyr Thr Pro Pro Ala Met Ile Phe Gln Thr Asn Gly Gln
                85                  90                  95

Val Thr Pro Trp Leu Arg Tyr Ala Glu Trp Leu Leu Thr Cys Pro Val
            100                 105                 110

Ile Leu Ile His Leu Ser Asn Ile Thr Gly Leu Asn Asp Asp Tyr Ser
        115                 120                 125

Gly Arg Thr Met Ser Leu Ile Thr Ser Asp Leu Gly Gly Ile Cys Met
    130                 135                 140

Ala Val Thr Ala Ala Leu Ser Lys Gly Trp Leu Lys Ala Leu Phe Phe
145                 150                 155                 160

Val Ile Gly Cys Gly Tyr Gly Ala Ser Thr Phe Tyr Asn Ala Ala Cys
                165                 170                 175

Ile Tyr Ile Glu Ser Tyr Tyr Thr Met Pro Gln Gly Ile Cys Arg Arg
                180                 185                 190

Leu Val Leu Trp Met Ala Gly Val Phe Phe Thr Ser Trp Phe Met Phe
            195                 200                 205

Pro Gly Leu Phe Leu Ala Gly Pro Glu Gly Thr Gln Ala Leu Ser Trp
210                 215                 220

Ala Gly Thr Thr Ile Gly His Thr Val Ala Asp Leu Leu Ser Lys Asn
225                 230                 235                 240

Ala Trp Gly Met Ile Gly His Phe Leu Arg Val Glu Ile His Lys His
                245                 250                 255

Ile Ile Ile His Gly Asp Val Arg Arg Pro Val Thr Val Lys Ala Leu
            260                 265                 270
```

```
Gly Arg Gln Val Ser Val Asn Cys Phe Val Asp Lys Glu Glu Glu
        275                 280                 285

Glu Asp Glu Arg Ile
    290
```

<210> SEQ ID NO 4
<211> LENGTH: 354
<212> TYPE: PRT
<213> ORGANISM: Artificial Sequence
<220> FEATURE:
<223> OTHER INFORMATION: Fusion protein having Volvox ChR1, N-terminus
      reagion of Chlamydomonas ChR1 and C-terminus reagion of
      Chlamydomonas ChR2 with C166A, D194C and H229N

<400> SEQUENCE: 4

```
Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
50                  55                  60

Ile Cys Met Pro Arg Gly Gln Cys Tyr Cys Glu Gly Trp Leu Arg Ser
65                  70                  75                  80

Arg Gly Thr Ser Ile Glu Lys Thr Ile Ala Ile Thr Leu Gln Trp Val
                85                  90                  95

Val Phe Ala Leu Ser Val Ala Cys Leu Gly Trp Tyr Ala Tyr Gln Ala
            100                 105                 110

Trp Arg Ala Thr Cys Gly Trp Glu Glu Val Tyr Val Ala Leu Ile Glu
        115                 120                 125

Met Met Lys Ser Ile Ile Glu Ala Phe His Glu Phe Asp Ser Pro Ala
130                 135                 140

Thr Leu Trp Leu Ser Ser Gly Asn Gly Val Val Trp Met Arg Tyr Gly
145                 150                 155                 160

Glu Trp Leu Leu Thr Ala Pro Val Leu Leu Ile His Leu Ser Asn Leu
                165                 170                 175

Thr Gly Leu Lys Asp Asp Tyr Ser Lys Arg Thr Met Gly Leu Leu Val
            180                 185                 190

Ser Cys Val Gly Cys Ile Val Trp Gly Ala Thr Ser Ala Met Cys Thr
        195                 200                 205

Gly Trp Thr Lys Ile Leu Phe Phe Leu Ile Ser Leu Ser Tyr Gly Met
210                 215                 220

Tyr Thr Tyr Phe Asn Ala Ala Lys Val Tyr Ile Glu Ala Phe His Thr
225                 230                 235                 240

Val Pro Lys Gly Ile Cys Arg Glu Leu Val Arg Val Met Ala Trp Thr
                245                 250                 255

Phe Phe Val Ala Trp Gly Met Phe Pro Val Leu Phe Leu Leu Gly Thr
            260                 265                 270

Glu Gly Phe Gly His Ile Ser Pro Tyr Gly Ser Ala Ile Gly His Ser
        275                 280                 285

Ile Leu Asp Leu Ile Ala Lys Asn Met Trp Gly Val Leu Gly Asn Tyr
290                 295                 300

Leu Arg Val Leu Ile His Glu His Ile Leu Ile His Gly Asp Ile Arg
305                 310                 315                 320
```

Lys Thr Thr Lys Leu Asn Ile Gly Gly Thr Glu Ile Glu Val Glu Thr
                325                 330                 335

Leu Val Glu Asp Glu Ala Glu Ala Gly Ala Val Asn Lys Gly Thr Gly
                340                 345                 350

Lys Asp

<210> SEQ ID NO 5
<211> LENGTH: 348
<212> TYPE: PRT
<213> ORGANISM: Artificial Sequence
<220> FEATURE:
<223> OTHER INFORMATION: Fusion protein having Volvox ChR1, N-terminus
      reagion of Chlamydomonas ChR1 and C-terminus reagion of
      Tetraselmis ChR with C166A, D194C and H229N

<400> SEQUENCE: 5

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Met Pro Arg Gly Gln Cys Tyr Cys Glu Gly Trp Leu Arg Ser
65                  70                  75                  80

Arg Gly Thr Ser Ile Glu Lys Thr Ile Ala Ile Thr Leu Gln Trp Val
                85                  90                  95

Val Phe Ala Leu Ser Val Ala Cys Leu Gly Trp Tyr Ala Tyr Gln Ala
            100                 105                 110

Trp Arg Ala Thr Cys Gly Trp Glu Glu Val Tyr Val Ala Leu Ile Glu
        115                 120                 125

Met Met Lys Ser Ile Ile Glu Ala Phe His Glu Phe Asp Ser Pro Ala
    130                 135                 140

Thr Leu Trp Leu Ser Ser Gly Asn Gly Val Val Trp Met Arg Tyr Gly
145                 150                 155                 160

Glu Trp Leu Leu Thr Ala Pro Val Leu Leu Ile His Leu Ser Asn Leu
                165                 170                 175

Thr Gly Leu Lys Asp Asp Tyr Ser Lys Arg Thr Met Gly Leu Leu Val
            180                 185                 190

Ser Cys Val Gly Cys Ile Val Trp Gly Ala Thr Ser Ala Met Cys Thr
        195                 200                 205

Gly Trp Thr Lys Ile Leu Phe Phe Leu Ile Ser Leu Ser Tyr Gly Met
    210                 215                 220

Tyr Thr Tyr Phe Asn Ala Ala Lys Val Tyr Ile Glu Ala Phe His Thr
225                 230                 235                 240

Val Pro Lys Gly Ile Cys Arg Glu Leu Val Arg Val Met Ala Trp Thr
                245                 250                 255

Phe Phe Val Ala Trp Gly Met Phe Pro Val Leu Phe Leu Leu Gly Thr
            260                 265                 270

Glu Gly Phe Gly His Ile Ser Pro Tyr Gly Ser Ala Ile Gly His Ser
        275                 280                 285

Ile Leu Asp Leu Ile Ala Lys Asn Met Trp Gly Val Leu Gly Asn Tyr
    290                 295                 300

Leu Arg Val Glu Ile His Lys His Ile Ile His Gly Asp Val Arg
305                 310                 315                 320

```
Arg Pro Val Thr Val Lys Ala Leu Gly Arg Gln Val Ser Val Asn Cys
                325                 330                 335

Phe Val Asp Lys Glu Glu Glu Glu Asp Glu Arg
            340                 345

<210> SEQ ID NO 6
<211> LENGTH: 712
<212> TYPE: PRT
<213> ORGANISM: Chlamydomonas reinhardtii

<400> SEQUENCE: 6

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
210                 215                 220

Ile Tyr Thr Phe Phe Asn Ala Ala Lys Val Tyr Ile Glu Ala Tyr His
225                 230                 235                 240

Thr Val Pro Lys Gly Ile Cys Arg Asp Leu Val Arg Tyr Leu Ala Trp
                245                 250                 255

Leu Tyr Phe Cys Ser Trp Ala Met Phe Pro Val Leu Phe Leu Leu Gly
            260                 265                 270

Pro Glu Gly Phe Gly His Ile Asn Gln Phe Asn Ser Ala Ile Ala His
        275                 280                 285

Ala Ile Leu Asp Leu Ala Ser Lys Asn Ala Trp Ser Met Met Gly His
290                 295                 300

Phe Leu Arg Val Lys Ile His Glu His Ile Leu Leu Tyr Gly Asp Ile
305                 310                 315                 320

Arg Lys Lys Gln Lys Val Asn Val Ala Gly Gln Glu Met Glu Val Glu
                325                 330                 335

Thr Met Val His Glu Glu Asp Asp Glu Thr Gln Lys Val Pro Thr Ala
```

```
            340                 345                 350
Lys Tyr Ala Asn Arg Asp Ser Phe Ile Ile Met Arg Asp Arg Leu Lys
            355                 360                 365
Glu Lys Gly Phe Glu Thr Arg Ala Ser Leu Asp Gly Asp Pro Asn Gly
            370                 375                 380
Asp Ala Glu Ala Asn Ala Ala Gly Gly Lys Pro Gly Met Glu Met
385                 390                 395                 400
Gly Lys Met Thr Gly Met Gly Met Gly Met Gly Ala Gly Met Gly Met
            405                 410                 415
Ala Thr Ile Asp Ser Gly Arg Val Ile Leu Ala Val Pro Asp Ile Ser
            420                 425                 430
Met Val Asp Phe Phe Arg Glu Gln Phe Ala Arg Leu Pro Val Pro Tyr
            435                 440                 445
Glu Leu Val Pro Ala Leu Gly Ala Glu Asn Thr Leu Gln Leu Val Gln
            450                 455                 460
Gln Ala Gln Ser Leu Gly Gly Cys Asp Phe Val Leu Met His Pro Glu
465                 470                 475                 480
Phe Leu Arg Asp Arg Ser Pro Thr Gly Leu Leu Pro Arg Leu Lys Met
            485                 490                 495
Gly Gly Gln Arg Ala Ala Ala Phe Gly Trp Ala Ala Ile Gly Pro Met
            500                 505                 510
Arg Asp Leu Ile Glu Gly Ser Gly Val Asp Gly Trp Leu Glu Gly Pro
            515                 520                 525
Ser Phe Gly Ala Gly Ile Asn Gln Gln Ala Leu Val Ala Leu Ile Asn
            530                 535                 540
Arg Met Gln Gln Ala Lys Lys Met Gly Met Met Gly Gly Met Gly Met
545                 550                 555                 560
Gly Met Gly Gly Gly Met Gly Met Gly Met Gly Met Gly Met Gly Met
            565                 570                 575
Ala Pro Ser Met Asn Ala Gly Met Thr Gly Gly Met Gly Gly Ala Ser
            580                 585                 590
Met Gly Gly Ala Val Met Gly Met Gly Met Gly Met Gln Pro Met Gln
            595                 600                 605
Gln Ala Met Pro Ala Met Ser Pro Met Met Thr Gln Gln Pro Ser Met
            610                 615                 620
Met Ser Gln Pro Ser Ala Met Ser Ala Gly Gly Ala Met Gln Ala Met
625                 630                 635                 640
Gly Gly Val Met Pro Ser Pro Ala Pro Gly Gly Arg Val Gly Thr Asn
            645                 650                 655
Pro Leu Phe Gly Ser Ala Pro Ser Pro Leu Ser Ser Gln Pro Gly Ile
            660                 665                 670
Ser Pro Gly Met Ala Thr Pro Pro Ala Ala Thr Ala Ala Pro Ala Ala
            675                 680                 685
Gly Gly Ser Glu Ala Glu Met Leu Gln Gln Leu Met Ser Glu Ile Asn
            690                 695                 700
Arg Leu Lys Asn Glu Leu Gly Glu
705                 710

<210> SEQ ID NO 7
<211> LENGTH: 354
<212> TYPE: PRT
<213> ORGANISM: Artificial Sequence
<220> FEATURE:
<223> OTHER INFORMATION: Fusion protein having Volvox ChR1 (provided
      that transmembrane domain 3 residue is replaced by that of
```

Chlamydomonas ChR1), N-terminus reagion of Chlamydomonas ChR1 and
C-terminus reagion of Chlamydomonas ChR2 with C166A, D194C and
H229N

<400> SEQUENCE: 7

| | | | | | | | | | | | | | | |
|---|---|---|---|---|---|---|---|---|---|---|---|---|---|---|
| Met | Ser | Arg | Arg | Pro | Trp | Leu | Leu | Ala | Leu | Ala | Leu | Ala | Val | Ala | Leu |
| 1 | | | | 5 | | | | | 10 | | | | | 15 | |
| Ala | Ala | Gly | Ser | Ala | Gly | Ala | Ser | Thr | Gly | Ser | Asp | Ala | Thr | Val | Pro |
| | | | 20 | | | | | 25 | | | | | 30 | | |
| Val | Ala | Thr | Gln | Asp | Gly | Pro | Asp | Tyr | Val | Phe | His | Arg | Ala | His | Glu |
| | | 35 | | | | | 40 | | | | | 45 | | | |
| Arg | Met | Leu | Phe | Gln | Thr | Ser | Tyr | Thr | Leu | Glu | Asn | Asn | Gly | Ser | Val |
| 50 | | | | | 55 | | | | | 60 | | | | | |
| Ile | Cys | Met | Pro | Arg | Gly | Gln | Cys | Tyr | Cys | Glu | Gly | Trp | Leu | Arg | Ser |
| 65 | | | | 70 | | | | | 75 | | | | | 80 | |
| Arg | Gly | Thr | Ser | Ile | Glu | Lys | Thr | Ile | Ala | Ile | Thr | Leu | Gln | Trp | Val |
| | | | 85 | | | | | 90 | | | | | 95 | | |
| Val | Phe | Ala | Leu | Ser | Val | Ala | Cys | Leu | Gly | Trp | Tyr | Ala | Tyr | Gln | Ala |
| | | 100 | | | | | 105 | | | | | 110 | | | |
| Trp | Arg | Ala | Thr | Cys | Gly | Trp | Glu | Glu | Val | Tyr | Val | Ala | Leu | Ile | Glu |
| | | 115 | | | | | 120 | | | | | 125 | | | |
| Met | Met | Lys | Ser | Ile | Ile | Glu | Ala | Phe | His | Glu | Phe | Asp | Glu | Pro | Ala |
| 130 | | | | | 135 | | | | | 140 | | | | | |
| Val | Ile | Tyr | Ser | Ser | Asn | Gly | Asn | Lys | Thr | Val | Trp | Leu | Arg | Tyr | Ala |
| 145 | | | | | 150 | | | | | 155 | | | | | 160 |
| Glu | Trp | Leu | Leu | Thr | Ala | Pro | Val | Ile | Leu | Ile | His | Leu | Ser | Asn | Leu |
| | | | | 165 | | | | | 170 | | | | | 175 | |
| Thr | Gly | Leu | Lys | Asp | Asp | Tyr | Ser | Lys | Arg | Thr | Met | Gly | Leu | Leu | Val |
| | | | 180 | | | | | 185 | | | | | 190 | | |
| Ser | Cys | Val | Gly | Cys | Ile | Val | Trp | Gly | Ala | Thr | Ser | Ala | Met | Cys | Thr |
| | | 195 | | | | | 200 | | | | | 205 | | | |
| Gly | Trp | Thr | Lys | Ile | Leu | Phe | Phe | Leu | Ile | Ser | Leu | Ser | Tyr | Gly | Met |
| | 210 | | | | | 215 | | | | | 220 | | | | |
| Tyr | Thr | Tyr | Phe | Asn | Ala | Ala | Lys | Val | Tyr | Ile | Glu | Ala | Phe | His | Thr |
| 225 | | | | | 230 | | | | | 235 | | | | | 240 |
| Val | Pro | Lys | Gly | Ile | Cys | Arg | Glu | Leu | Val | Arg | Val | Met | Ala | Trp | Thr |
| | | | | 245 | | | | | 250 | | | | | 255 | |
| Phe | Phe | Val | Ala | Trp | Gly | Met | Phe | Pro | Val | Leu | Phe | Leu | Leu | Gly | Thr |
| | | | 260 | | | | | 265 | | | | | 270 | | |
| Glu | Gly | Phe | Gly | His | Ile | Ser | Pro | Tyr | Gly | Ser | Ala | Ile | Gly | His | Ser |
| | | 275 | | | | | 280 | | | | | 285 | | | |
| Ile | Leu | Asp | Leu | Ile | Ala | Lys | Asn | Met | Trp | Gly | Val | Leu | Gly | Asn | Tyr |
| | 290 | | | | | 295 | | | | | 300 | | | | |
| Leu | Arg | Val | Leu | Ile | His | Glu | His | Ile | Leu | Ile | His | Gly | Asp | Ile | Arg |
| 305 | | | | | 310 | | | | | 315 | | | | | 320 |
| Lys | Thr | Thr | Lys | Leu | Asn | Ile | Gly | Gly | Thr | Glu | Ile | Glu | Val | Glu | Thr |
| | | | | 325 | | | | | 330 | | | | | 335 | |
| Leu | Val | Glu | Asp | Glu | Ala | Glu | Ala | Gly | Ala | Val | Asn | Lys | Gly | Thr | Gly |
| | | | 340 | | | | | 345 | | | | | 350 | | |
| Lys | Asp | | | | | | | | | | | | | | |

<210> SEQ ID NO 8
<211> LENGTH: 349
<212> TYPE: PRT
<213> ORGANISM: Artificial Sequence
<220> FEATURE:
<223> OTHER INFORMATION: Fusion protein having Volvox ChR1 (provided that transmembrane domain 3 residue is replaced by that of Chlamydomonas ChR1), N-terminus reagion of Chlamydomonas ChR1 and C-terminus reagion of Tetraselmis ChR with C166A, D194C and H229N

<400> SEQUENCE: 8

```
Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
50                  55                  60

Ile Cys Met Pro Arg Gly Gln Cys Tyr Cys Glu Gly Trp Leu Arg Ser
65                  70                  75                  80

Arg Gly Thr Ser Ile Glu Lys Thr Ile Ala Ile Thr Leu Gln Trp Val
                85                  90                  95

Val Phe Ala Leu Ser Val Ala Cys Leu Gly Trp Tyr Ala Tyr Gln Ala
            100                 105                 110

Trp Arg Ala Thr Cys Gly Trp Glu Glu Val Tyr Val Ala Leu Ile Glu
            115                 120                 125

Met Met Lys Ser Ile Ile Glu Ala Phe His Glu Phe Asp Glu Pro Ala
130                 135                 140

Val Ile Tyr Ser Ser Asn Gly Asn Lys Thr Val Trp Leu Arg Tyr Ala
145                 150                 155                 160

Glu Trp Leu Leu Thr Ala Pro Val Ile Leu Ile His Leu Ser Asn Leu
                165                 170                 175

Thr Gly Leu Lys Asp Asp Tyr Ser Lys Arg Thr Met Gly Leu Leu Val
            180                 185                 190

Ser Cys Val Gly Cys Ile Val Trp Gly Ala Thr Ser Ala Met Cys Thr
            195                 200                 205

Gly Trp Thr Lys Ile Leu Phe Phe Leu Ile Ser Leu Ser Tyr Gly Met
210                 215                 220

Tyr Thr Tyr Phe Asn Ala Ala Lys Val Tyr Ile Glu Ala Phe His Thr
225                 230                 235                 240

Val Pro Lys Gly Ile Cys Arg Glu Leu Val Arg Val Met Ala Trp Thr
                245                 250                 255

Phe Phe Val Ala Trp Gly Met Phe Pro Val Leu Phe Leu Leu Gly Thr
            260                 265                 270

Glu Gly Phe Gly His Ile Ser Pro Tyr Gly Ser Ala Ile Gly His Ser
            275                 280                 285

Ile Leu Asp Leu Ile Ala Lys Asn Met Trp Gly Val Leu Gly Asn Tyr
290                 295                 300

Leu Arg Val Glu Ile His Lys His Ile Ile His Gly Asp Val Arg
305                 310                 315                 320

Arg Pro Val Thr Val Lys Ala Leu Gly Arg Gln Val Ser Val Asn Cys
                325                 330                 335

Phe Val Asp Lys Glu Glu Glu Glu Asp Glu Arg Asp
            340                 345
```

<210> SEQ ID NO 9
<211> LENGTH: 354
<212> TYPE: PRT
<213> ORGANISM: Artificial Sequence
<220> FEATURE:
<223> OTHER INFORMATION: Fusion protein having Volvox ChR1 (provided
that transmembrane domain 3 residue is replaced by that of
Chlamydomonas ChR1), N-terminus reagion of Chlamydomonas ChR1 and
C-terminus reagion of Chlamydomonas ChR2 with E161T, C166A, D194C
and H229N

<400> SEQUENCE: 9

```
Met Ser Arg Arg Pro Trp Leu Leu Ala Leu Ala Leu Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
    50                  55                  60

Ile Cys Met Pro Arg Gly Gln Cys Tyr Cys Glu Gly Trp Leu Arg Ser
65                  70                  75                  80

Arg Gly Thr Ser Ile Glu Lys Thr Ile Ala Ile Thr Leu Gln Trp Val
                85                  90                  95

Val Phe Ala Leu Ser Val Ala Cys Leu Gly Trp Tyr Ala Tyr Gln Ala
            100                 105                 110

Trp Arg Ala Thr Cys Gly Trp Glu Glu Val Tyr Val Ala Leu Ile Glu
            115                 120                 125

Met Met Lys Ser Ile Ile Glu Ala Phe His Glu Phe Asp Glu Pro Ala
    130                 135                 140

Val Ile Tyr Ser Ser Asn Gly Asn Lys Thr Val Trp Leu Arg Tyr Ala
145                 150                 155                 160

Thr Trp Leu Leu Thr Ala Pro Val Ile Leu Ile His Leu Ser Asn Leu
                165                 170                 175

Thr Gly Leu Lys Asp Asp Tyr Ser Lys Arg Thr Met Gly Leu Leu Val
            180                 185                 190

Ser Cys Val Gly Cys Ile Val Trp Gly Ala Thr Ser Ala Met Cys Thr
            195                 200                 205

Gly Trp Thr Lys Ile Leu Phe Phe Leu Ile Ser Leu Ser Tyr Gly Met
    210                 215                 220

Tyr Thr Tyr Phe Asn Ala Ala Lys Val Tyr Ile Glu Ala Phe His Thr
225                 230                 235                 240

Val Pro Lys Gly Ile Cys Arg Glu Leu Val Arg Val Met Ala Trp Thr
                245                 250                 255

Phe Phe Val Ala Trp Gly Met Phe Pro Val Leu Phe Leu Leu Gly Thr
            260                 265                 270

Glu Gly Phe Gly His Ile Ser Pro Tyr Gly Ser Ala Ile Gly His Ser
            275                 280                 285

Ile Leu Asp Leu Ile Ala Lys Asn Met Trp Gly Val Leu Gly Asn Tyr
    290                 295                 300

Leu Arg Val Leu Ile His Glu His Ile Leu Ile His Gly Asp Ile Arg
305                 310                 315                 320

Lys Thr Thr Lys Leu Asn Ile Gly Gly Thr Glu Ile Glu Val Glu Thr
                325                 330                 335

Leu Val Glu Asp Glu Ala Glu Ala Gly Ala Val Asn Lys Gly Thr Gly
            340                 345                 350

Lys Asp
```

<210> SEQ ID NO 10

<211> LENGTH: 343
<212> TYPE: PRT
<213> ORGANISM: Artificial Sequence
<220> FEATURE:
<223> OTHER INFORMATION: Fusion protein having Volvox ChR1 (provided
   that transmembrane domain 3 residue is replaced by that of
   Chlamydomonas ChR1) and N-terminus reagion of Chlamydomonas ChR1

<400> SEQUENCE: 10

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Met Pro Arg Gly Gln Cys Tyr Cys Glu Gly Trp Leu Arg Ser
65                  70                  75                  80

Arg Gly Thr Ser Ile Glu Lys Thr Ile Ala Ile Thr Leu Gln Trp Val
                85                  90                  95

Val Phe Ala Leu Ser Val Ala Cys Leu Gly Trp Tyr Ala Tyr Gln Ala
            100                 105                 110

Trp Arg Ala Thr Cys Gly Trp Glu Glu Val Tyr Val Ala Leu Ile Glu
        115                 120                 125

Met Met Lys Ser Ile Ile Glu Ala Phe His Glu Phe Asp Glu Pro Ala
    130                 135                 140

Val Ile Tyr Ser Ser Asn Gly Asn Lys Thr Val Trp Leu Arg Tyr Ala
145                 150                 155                 160

Glu Trp Leu Leu Thr Cys Pro Val Ile Leu Ile His Leu Ser Asn Leu
                165                 170                 175

Thr Gly Leu Lys Asp Asp Tyr Ser Lys Arg Thr Met Gly Leu Leu Val
            180                 185                 190

Ser Asp Val Gly Cys Ile Val Trp Gly Ala Thr Ser Ala Met Cys Thr
        195                 200                 205

Gly Trp Thr Lys Ile Leu Phe Phe Leu Ile Ser Leu Ser Tyr Gly Met
    210                 215                 220

Tyr Thr Tyr Phe His Ala Ala Lys Val Tyr Ile Glu Ala Phe His Thr
225                 230                 235                 240

Val Pro Lys Gly Ile Cys Arg Glu Leu Val Arg Val Met Ala Trp Thr
                245                 250                 255

Phe Phe Val Ala Trp Gly Met Phe Pro Val Leu Phe Leu Leu Gly Thr
            260                 265                 270

Glu Gly Phe Gly His Ile Ser Pro Tyr Gly Ser Ala Ile Gly His Ser
        275                 280                 285

Ile Leu Asp Leu Ile Ala Lys Asn Met Trp Gly Val Leu Gly Asn Tyr
    290                 295                 300

Leu Arg Val Lys Ile His Glu His Ile Leu Leu Tyr Gly Asp Ile Arg
305                 310                 315                 320

Lys Lys Gln Lys Ile Thr Ile Ala Gly Gln Glu Met Glu Val Glu Thr
                325                 330                 335

Leu Val Ala Glu Glu Asp
            340

<210> SEQ ID NO 11
<211> LENGTH: 1064

<212> TYPE: DNA
<213> ORGANISM: Artificial Sequence
<220> FEATURE:
<223> OTHER INFORMATION: DNA encoding fusion protein having Volvox ChR1,
    N-terminus reagion of Chlamydomonas ChR1 and C-terminus region of
    Chlamydomonas ChR2 with C166A, D194C and H229N

<400> SEQUENCE: 11

```
atgagcagaa ggccttggct gcttgctctg ctctggctg ttgcacttgc tgctggatct      60
gctggcgcct ctacaggatc tgatgctaca gtgccagtgg ccacacagga cggccctgat     120
tatgtgtttc acagagccca cgagcggatg ctgttccaga ccagctacac cctggaaaac    180
aacggcagcg tgatctgcat gcccagaggc cagtgttact gcgaaggctg gctgagaagc    240
agaggcacca gcatcgagaa aacaatcgcc atcactctgc agtgggtcgt gtttgccctg    300
tctgtggcct gtctcggatg gtacgcttac caggcttgga gagccacctg tggctgggaa    360
gaagtgtacg tcgccctgat cgagatgatg aagtccatca tcgaggcctt ccacgagttc    420
gactctcccg ctacactgtg gctgtctagc ggaaatggcg tcgtgtggat gagatacggc    480
gagtggctgc tgacagcccc tgtgctgctg atccacctgt ctaatctgac cggcctgaag    540
gacgactaca gcaagagaac aatgggcctg ctggtgtcct gcgtgggatg tattgtgtgg    600
ggagccacct tgccatgtg taccggatgg accaagatcc tgttcttcct gatcagcctg    660
agctacggca tgtacaccta cttcaacgcc gccaaagtgt acattgaggc ctttcacacc    720
gtgcctaagg gcatctgcag agaactcgtc cgcgtgatgg cctggacctt ttttgtggcc    780
tggggaatgt tccccgtgct gtttctgctg ggcaccgaag gctttggcca catctctcca    840
tatggcagcg ccatcggcca cagcatcctg gacctgatcg ccaagaatat gtggggcgtg    900
ctgggcaact acctgcgggt gctgattcac gagcacatcc tgatccacgg cgacatcaga    960
aagaccacca agctgaatat cggcggcacc gagatcgagg tggaaaccct ggtggaagat   1020
gaagctgaag ccggcgctgt gaacaaaggc actggaaagg atcc                    1064
```

<210> SEQ ID NO 12
<211> LENGTH: 1044
<212> TYPE: DNA
<213> ORGANISM: Artificial Sequence
<220> FEATURE:
<223> OTHER INFORMATION: DNA encoding fusion protein having Volvox ChR1,
    N-terminus reagion of Chlamydomonas ChR1 and C-terminus reagion of
    Tetraselmis ChR with C166A, D194C and H229N

<400> SEQUENCE: 12

```
atgagcagaa ggccttggct gcttgctctg ctctggctg ttgcacttgc tgctggatct      60
gctggcgcct ctacaggatc tgatgctaca gtgccagtgg ccacacagga cggccctgat    120
tatgtgtttc acagagccca cgagcggatg ctgttccaga ccagctacac cctggaaaac   180
aacggcagcg tgatctgcat gcccagaggc cagtgttact gcgaaggctg gctgagaagc   240
agaggcacca gcatcgagaa aacaatcgcc atcactctgc agtgggtcgt gtttgccctg   300
tctgtggcct gtctcggatg gtacgcttac caggcttgga gagccacctg tggctgggaa   360
gaagtgtacg tcgccctgat cgagatgatg aagtccatca tcgaggcctt ccacgagttc   420
gactctcccg ctacactgtg gctgtctagc ggaaatggcg tcgtgtggat gagatacggc   480
gagtggctgc tgacagcccc tgtgctgctg atccacctgt ctaatctgac cggcctgaag   540
gacgactaca gcaagagaac aatgggcctg ctggtgtcct gcgtgggatg tattgtgtgg   600
ggagccacct tgccatgtg taccggatgg accaagatcc tgttcttcct gatcagcctg   660
```

```
agctacggca tgtacaccta cttcaacgcc gccaaagtgt acattgaggc ctttcacacc    720
gtgcctaagg gcatctgcag agaactcgtc cgcgtgatgg cctggacctt ttttgtggcc    780
tggggaatgt tccccgtgct gtttctgctg ggcaccgaag ctttggcca catctctcca     840 tatggcagcg ccatcggcca cagcatcctg gacctgatcg ccaagaatat gtggggcgtg    900
ctgggcaact acctgcgggt ggagatccac aagcatatca tcatccatgg agatgtgcgg    960
cgccccgtga cagtgaaggc tctggggagg caggtgagcg tgaattgttt cgtggacaaa   1020
gaggaagagg aagaggatga gaga                                           1044
```

<210> SEQ ID NO 13
<211> LENGTH: 1064
<212> TYPE: DNA
<213> ORGANISM: Artificial Sequence
<220> FEATURE:
<223> OTHER INFORMATION: DNA encoding fusion protein having Volvox ChR1
      (provided that transmembrane domain 3 residue is replaced by that
      of Chlamydomonas ChR1), N-terminus region of Chlamydomonas ChR1
      and C-terminus region of Chlamydomonas ChR2 with C166A, D194C and
      H229N

<400> SEQUENCE: 13

```
atgagcagaa ggccttggct gctggctctg gcactggctg ttgctcttgc tgctggatct     60
gccggcgcta gcacaggatc tgatgctaca gtgccagtgg ccacacagga cggccctgac   120
tatgtgtttc acagagccca cgagcggatg ctgttccaga ccagctacac cctgaaaaac   180
aacggcagcg tgatctgcat gcccagaggc cagtgttact gcgaaggctg gctgagaagc   240
agaggcacca gcatcgagaa aacaatcgcc atcactctgc agtgggtcgt gttcgccctg   300
tctgtggctt gtcttggatg gtacgcctat caggcctggc gggctacatg tggatgggaa   360
gaagtgtacg tcgccctgat cgagatgatg aagtccatca tcgaggcctt ccacgagttc   420
gacgagcccg ccgtgatcta cagctccaac ggcaacaaga ccgtgtggct gagatacgcc   480
gagtggctgc tgacagcccc ctgtgatcct atccacctga gcaatctgac cggcctgaag   540
gacgactaca gcaagagaac catgggcctg ctggtgtcct gcgtgggatg tattgtgtgg    600
ggagccacca cgccatgtg taccggatgg accaagatcc tgttcttcct gatcagcctg    660
tcctacggca tgtacaccta cttcaacgcc gccaaagtgt acattgaggc ctttcacacc   720
gtgcctaagg gcatctgccg ggaactcgtc agagtcatgg cctggacctt ttcgtggcc    780 tggggaatgt tccccgtgct gtttctgctg ggcaccgaag ctttggcca catcagccct    840 tatggctctg ccatcggcca cagcatcctg gacctgatcg ccaagaatat gtggggcgtg   900
ctgggcaact acctgagagt gctgattcac gagcacatcc tgatccacgg cgacatcaga  960
aagaccacca gctgaatat cggcggcacc gagatcgagg tggaaaccct ggtggaagat    1020
gaagctgaag ccggcgctgt gaacaaaggc actggaaagg atcc                    1064
```

<210> SEQ ID NO 14
<211> LENGTH: 1037
<212> TYPE: DNA
<213> ORGANISM: Artificial Sequence
<220> FEATURE:
<223> OTHER INFORMATION: DNA encoding fusion protein having Volvox ChR1
      (provided that transmembrane domain 3 residue is replaced by that
      of Chlamydomonas ChR1), N-terminus region of Chlamydomonas ChR1
      and C-terminus region of Tetraselmis ChR with C166A, D194C and
      H229N

<400> SEQUENCE: 14

```
atgagcagaa ggccttggct gctggctctg gcactggctg ttgctcttgc tgctggatct     60
```

```
gccggcgcta gcacaggatc tgatgctaca gtgccagtgg ccacacagga cggccctgac    120
tatgtgtttc acagagccca cgagcggatg ctgttccaga ccagctacac cctggaaaac    180
aacggcagcg tgatctgcat gcccagaggc cagtgttact gcgaaggctg gctgagaagc    240
agaggcacca gcatcgagaa aacaatcgcc atcactctgc agtgggtcgt gttcgccctg    300
tctgtggctt gtcttggatg gtacgcctat caggcctggc gggctacatg tggatgggaa    360
gaagtgtacg tcgccctgat cgagatgatg aagtccatca tcgaggcctt ccacgagttc    420
gacgagcccg ccgtgatcta cagctccaac ggcaacaaga ccgtgtggct gagatacgcc    480
gagtggctgc tgacagcccc tgtgatcctg atccacctga gcaatctgac cggcctgaag    540
gacgactaca gcaagagaac catgggcctg ctggtgtcct gcgtgggatg tattgtgtgg    600
ggagccacca gcgccatgtg taccggatgg accaagatcc tgttcttcct gatcagcctg    660
tcctacggca tgtacaccta cttcaacgcc gccaaagtgt acattgaggc ctttcacacc    720
gtgcctaagg gcatctgccg ggaactcgtc agagtcatgg cctggacctt tttcgtggcc    780
tggggaatgt tccccgtgct gtttctgctg ggcaccgaag gctttggcca catcagccct    840
tatggctctg ccatcggcca cagcatcctg gacctgatcg ccaagaatat gtggggcgtg    900
ctgggcaact acctgagagt gaagatccac gagcacatcc tgctgtacgg cgacatccgg    960
aagaagcaga agatcacaat cgccggccaa gagatggaag tggaaaccct ggtggccgag   1020
gaagaggatc gggatcc                                                   1037
```

<210> SEQ ID NO 15
<211> LENGTH: 1064
<212> TYPE: DNA
<213> ORGANISM: Artificial Sequence
<220> FEATURE:
<223> OTHER INFORMATION: DNA encoding fusion protein having Volvox ChR1
    (provided that transmembrane domain 3 residue is replaced by that
    of Chlamydomonas ChR1), N-terminus reagion of Chlamydomonas ChR1
    and C-terminus reagion of Chlamydomonas ChR2 with E161T, C166A,
    D194C and H229N

<400> SEQUENCE: 15

```
atgagcagaa ggccttggct gctggctctg gcactggctg ttgctcttgc tgctggatct     60
gccggcgcta gcacaggatc tgatgctaca gtgccagtgg ccacacagga cggccctgac    120
tatgtgtttc acagagccca cgagcggatg ctgttccaga ccagctacac cctggaaaac    180
aacggcagcg tgatctgcat gcccagaggc cagtgttact gcgaaggctg gctgagaagc    240
agaggcacca gcatcgagaa aacaatcgcc atcactctgc agtgggtcgt gttcgccctg    300
tctgtggctt gtcttggatg gtacgcctat caggcctggc gggctacatg tggatgggaa    360
gaagtgtacg tcgccctgat cgagatgatg aagtccatca tcgaggcctt ccacgagttc    420
gacgagcccg ccgtgatcta cagctccaac ggcaacaaga ccgtgtggct gagatacgcc    480
acgtggctgc tgacagcccc tgtgatcctg atccacctga gcaatctgac cggcctgaag    540
gacgactaca gcaagagaac catgggcctg ctggtgtcct gcgtgggatg tattgtgtgg    600
ggagccacca gcgccatgtg taccggatgg accaagatcc tgttcttcct gatcagcctg    660
tcctacggca tgtacaccta cttcaacgcc gccaaagtgt acattgaggc ctttcacacc    720
gtgcctaagg gcatctgccg ggaactcgtc agagtcatgg cctggacctt tttcgtggcc    780
tggggaatgt tccccgtgct gtttctgctg ggcaccgaag gctttggcca catcagccct    840
tatggctctg ccatcggcca cagcatcctg gacctgatcg ccaagaatat gtggggcgtg    900
```

```
ctgggcaact acctgcgggt gctgattcac gagcacattc tgatccacgg cgacatcaga    960
aagaccacca agctgaacat cggcggcacc gagatcgagg tggaaaccct ggtggaagat   1020
gaggctgaag ccggcgctgt gaacaaaggc actggaaagg atcc                   1064
```

<210> SEQ ID NO 16
<211> LENGTH: 1029
<212> TYPE: DNA
<213> ORGANISM: Artificial Sequence
<220> FEATURE:
<223> OTHER INFORMATION: DNA encoding fusion protein having Volvox ChR1
    (provided that transmembrane domain 3 residue is replaced by that
    of Chlamydomonas ChR1) and N-terminus reagion of Chlamydomonas
    ChR1

<400> SEQUENCE: 16

```
atgtctagaa ggccttggct gcttgctctg gctctggctg ttgcacttgc tgctggatct     60
gctggcgcct ctacaggatc tgatgctaca gtgccagtgg ccacacagga cggccctgat    120
tatgtgtttc acagagccca cgagcggatg ctgttccaga ccagctacac cctggaaaac    180
aacggcagcg tgatctgcat gcccagaggc cagtgttact gcgaaggctg gctgagaagc    240
agaggcacca gcatcgagaa aacaatcgcc atcactctgc agtgggtcgt gtttgccctg    300
tctgtggcct gtctcggatg gtacgcttac caggcttgga gagccacctg tggctgggaa    360
gaagtgtacg tcgccctgat cgagatgatg aagtccatca tcgaggcctt ccacgagttc    420
gacgagcctg ccgtgatcta cagctccaac ggcaacaaga ccgtgtggct gagatatgcc    480
gagtggctgc tgacctgtcc tgtgatcctg atccacctga gcaacctgac cggcctgaag    540
gacgactaca gcaagagaac aatgggcctg ctggtgtccg atgtgggctg tattgtgtgg    600
ggagccacct ctgccatgtg taccggatgg accaagatcc tgttcttcct gatcagcctg    660
tcctacggca tgtacaccta cttccacgcc gccaaagtgt acattgaggc ctttcacacc    720
gtgcctaagg gcatctgcag agaactcgtc cgcgtgatgg cctggacctt ttttgtggcc    780
tggggaatgt tccccgtgct gtttctgctg ggcacagaag gctttggcca catcagccct    840
tatggctctg ccatcggcca cagcatcctg gacctgatcg ccaagaatat gtgggcgtg    900 ctgggcaact acctgagagt gaagatccac gagcacatcc tgctgtacgg cgacatccgg    960
aagaagcaga agatcacaat cgccggccaa gagatggaag tggaaaccct ggtggccgag   1020
gaagaggac                                                          1029
```

MODIFIED CHANNEL RHODOPSIN

TECHNICAL FIELD

The present invention relates to a modified channel rhodopsin. More specifically, it relates to a modified channel rhodopsin capable of opening and closing an ion channel by irradiation with light at different wavelengths, and/or having high ion permeability (photoreactivity).

BACKGROUND ART

It is well known that a research aiming at reconstruction of visual function by optogenetics to control cellular response by applying light to neurons made to express a photoresponsive protein (channel rhodopsin) by gene transfer has been globally performed, and the present inventors also have reported a modified channel rhodopsin whose expression efficiency on a cell membrane is improved by substituting an N-terminal region of a *Volvox carteri*-derived channel rhodopsin by an N-terminal region of a *Chlamydomonas reinhardtii*-derived channel rhodopsin-1 in Patent Document 1. The modified channel rhodopsin can induce excitement by opening an ion channel through application of light, and the present inventors have succeeded in restoring eyesight by introducing a gene thereof into the retina of a rat with visual loss.

However, neurons originally present in the retina have a function of performing excitement and its suppression by opening or closing an ion channel, and therefore, a modified channel rhodopsin closer to such an innate visual system has been demanded. Further, a modified channel rhodopsin having higher ion permeability than a previously reported modified channel rhodopsin has been demanded.

PRIOR ART DOCUMENTS

Patent Document
Patent Document 1: Japanese Patent No. 5322067

SUMMARY OF THE INVENTION

Problems that the Invention is to Solve

Therefore, an object of the present invention is to provide a modified channel rhodopsin capable of opening and closing an ion channel by irradiation with light at different wavelengths, and/or having high ion permeability.

Means for Solving the Problems

As a result of intensive studies in view of the above points, the present inventors have found that by substituting a C-terminal region of the modified channel rhodopsin reported by the present inventors in Patent Document 1 by a C-terminal region of a *Chlamydomonas reinhardtii*-derived channel rhodopsin-2 or a C-terminal region of a *Tetraselmis striata*-derived channel rhodopsin, a channel rhodopsin that opens an ion channel by irradiation with light in a wide wavelength range of visible light and closes the ion channel by irradiation with light at a shorter wavelength than the wavelength at which the ion channel is opened is obtained.

Further, the present inventors have found that by substituting the third transmembrane domain of seven transmembrane domains included in the modified channel rhodopsin reported by the present inventors in Patent Document 1 by the third transmembrane domain of seven transmembrane domains included in a *Chlamydomonas reinhardtii*-derived channel rhodopsin-1, a channel rhodopsin having high ion permeability is obtained.

A modified channel rhodopsin of the present invention achieved based on the above-mentioned findings is, as described in item 1, a polypeptide obtained by substituting a C-terminal region of a channel rhodopsin obtained by substituting an N-terminal region of a *Volvox carteri*-derived channel rhodopsin by an N-terminal region of a *Chlamydomonas reinhardtii*-derived channel rhodopsin-1, by a C-terminal region of a *Chlamydomonas reinhardtii*-derived channel rhodopsin-2, and is obtained by adding a C-terminal region of the *Chlamydomonas reinhardtii*-derived channel rhodopsin-2 containing at least amino acids at positions 270 to 315 in the amino acid sequence represented by SEQ ID NO: 2 to the C-terminus of a polypeptide containing at least amino acids at positions 1 to 307 in the amino acid sequence represented by SEQ ID NO: 1.

Further, a modified channel rhodopsin of the present invention is, as described in item 2, a polypeptide obtained by substituting a C-terminal region of a channel rhodopsin obtained by substituting an N-terminal region of a *Volvox carteri*-derived channel rhodopsin by an N-terminal region of a *Chlamydomonas reinhardtii*-derived channel rhodopsin-1, by a C-terminal region of a *Tetraselmis striata*-derived channel rhodopsin, and is obtained by adding a C-terminal region of the *Tetraselmis striata*-derived channel rhodopsin containing at least amino acids at positions 252 to 292 in the amino acid sequence represented by SEQ ID NO: 3 to the C-terminus of a polypeptide containing at least amino acids at positions 1 to 307 in the amino acid sequence represented by SEQ ID NO: 1.

Further, a modified channel rhodopsin described in item 3 is, in the modified channel rhodopsin described in item 1 or 2, obtained by substituting an amino acid (cysteine) at position 166 in the amino acid sequence represented by SEQ ID NO: 1 by alanine.

Further, a modified channel rhodopsin described in item4 is, in the modified channel rhodopsin described in item 3, any of the following (a) to (c):
(a) a polypeptide composed of the amino acid sequence represented by SEQ ID NO: 4;
(b) a polypeptide that is composed of an amino acid sequence including deletion, substitution, addition, or insertion of one or a plurality of amino acids in the amino acid sequence represented by SEQ ID NO: 4, and that has a biological activity equivalent to that of the polypeptide (a); and
(c) a polypeptide that is composed of an amino acid sequence having at least 90% sequence identity to the amino acid sequence represented by SEQ ID NO: 4, and that has a biological activity equivalent to that of the polypeptide (a).

Further, a modified channel rhodopsin described in item5 is, in the modified channel rhodopsin described in item 3, any of the following (a) to (c):
(a) a polypeptide composed of the amino acid sequence represented by SEQ ID NO: 5;
(b) a polypeptide that is composed of an amino acid sequence including deletion, substitution, addition, or insertion of one or a plurality of amino acids in the amino acid sequence represented by SEQ ID NO: 5, and that has a biological activity equivalent to that of the polypeptide (a); and
(c) a polypeptide that is composed of an amino acid sequence having at least 90' sequence identity to the amino acid sequence represented by SEQ ID NO: 5, and that has a biological activity equivalent to that of the polypeptide (a).

Further, a modified channel rhodopsin described in item 6 is, in the modified channel rhodopsin described in item 1 or 2, obtained by substituting amino acids at positions 142 to 169 in the amino acid sequence represented by SEQ ID NO: 1 by amino acids at positions 143 to 170 in the amino acid sequence of a *Chlamydomonas reinhardtii*-derived channel rhodopsin-1 represented by SEQ ID NO: 6.

Further, a modified channel rhodopsin described in item 7 is, in the modified channel rhodopsin described in item 6, obtained by substituting an amino acid (cysteine) at position 167 in the amino acid sequence represented by SEQ ID NO: 6 by alanine.

Further, a modified channel rhodopsin described in item 8 is, in the modified channel rhodopsin described in item 6 or 7, obtained by substituting an amino acid (glutamic acid) at position 162 in the amino acid sequence represented by SEQ ID NO: 6 by threonine.

Further, a modified channel rhodopsin described in item 9 is, in the modified channel rhodopsin described in item 7, any of the following (a) to (c):
  (a) a polypeptide composed of the amino acid sequence represented by SEQ ID NO: 7;
  (b) a polypeptide that is composed of an amino acid sequence including deletion, substitution, addition, or insertion of one or a plurality of amino acids in the amino acid sequence represented by SEQ ID NO: 7, and that has a biological activity equivalent to that of the polypeptide (a); and
  (c) a polypeptide that is composed of an amino acid sequence having at least 90% sequence identity to the amino acid sequence represented by SEQ ID NO: 7, and that has a biological activity equivalent to that of the polypeptide (a).

Further, a modified channel rhodopsin described in item 10 is, in the modified channel rhodopsin described in item 7, any of the following (a) to (c):
  (a) a polypeptide composed of the amino acid sequence represented by SEQ ID NO: 8;
  (b) a polypeptide that is composed of an amino acid sequence including deletion, substitution, addition, or insertion of one or a plurality of amino acids in the amino acid sequence represented by SEQ ID NO: 8, and that has a biological activity equivalent to that of the polypeptide (a); and
  (c) a polypeptide that is composed of an amino acid sequence having at least 90% sequence identity to the amino acid sequence represented by SEQ ID NO: 8, and that has a biological activity equivalent to that of the polypeptide (a).

Further, a modified channel rhodopsin described in item 11 is, in the modified channel rhodopsin described in item 8, any of the following (a) to (c):
  (a) a polypeptide composed of the amino acid sequence represented by SEQ ID NO: 9;
  (b) a polypeptide that is composed of an amino acid sequence including deletion, substitution, addition, or insertion of one or a plurality of amino acids in the amino acid sequence represented by SEQ ID NO: 9, and that has a biological activity equivalent to that of the polypeptide (a); and
  (c) a polypeptide that is composed of an amino acid sequence having at least 90% sequence identity to the amino acid sequence represented by SEQ ID NO: 9, and that has a biological activity equivalent to that of the polypeptide (a).

Further, a modified channel rhodopsin of the present invention is, as described in item 12, a polypeptide obtained by substituting the third transmembrane domain of seven transmembrane domains included in a channel rhodopsin obtained by substituting an N-terminal region of a *Volvox carteri*-derived channel rhodopsin by an N-terminal region of a *Chlamydomonas reinhardtii*-derived channel rhodopsin-1, by the third transmembrane domain of seven transmembrane domains included in the *Chlamydomonas reinhardtii*-derived channel rhodopsin-1, and is any of the following (a) to (c):
  (a) a polypeptide composed of the amino acid sequence represented by SEQ ID NO: 10;
  (b) a polypeptide that is composed of an amino acid sequence including deletion, substitution, addition, or insertion of one or a plurality of amino acids in the amino acid sequence represented by SEQ ID NO: 10, and that has a biological activity equivalent to that of the polypeptide (a); and
  (c) a polypeptide that is composed of an amino acid sequence having at least 90% sequence identity to the amino acid sequence represented by SEQ ID NO: 10, and that has a biological activity equivalent to that of the polypeptide (a).

Further, a polynucleotide of the present invention, as described in item 13, encodes the polypeptide described in any of items 1 to 12.

Further, an expression vector of the present invention, as described in item 14, includes the polynucleotide described in item 13 functionally linked to a promoter.

Further, a cell of the present invention, as described in item 15, expresses the polypeptide described in any of item 1 to 12.

Further, a cell described in item 16 is, in the cell described in item 15, a visual cell.

Further, the present invention is directed to, as described in item 17, use of any of the polypeptide described in any of items 1 to 12, the polynucleotide described in item 13, and the expression vector described in item 14 in the production of a pharmaceutical for treating a subject suffering from damage to the outer retinal layers.

Further, in use described in item 18, in the use described in item 17, the damage to the outer retinal layers is retinitis pigmentosa, age-related macular degeneration, or retinal detachment.

Further, a pharmaceutical composition for treating damage to the outer retinal layers of the present invention, as described in item 19, contains either the polypeptide described in any of item 1 to 12 or the expression vector described in item 14 as an active ingredient.

Effect of the Invention

According to the present invention, a modified channel rhodopsin capable of opening and closing an ion channel by irradiation with light at different wavelengths, and/or having high ion permeability can be provided.

BRIEF DESCRIPTION OF THE DRAWINGS

FIG. 1 A structure of a plasmid for preparing an adeno-associated virus vector expressing neomVChR1 in Example 1.

FIG. 2 Measurement results of a light-induced current by a patch clamp method in a cell expressing neomVChR1 in Example 1.

FIG. 3 Graphs showing that switCh has higher ion permeability than neomVChR1 in Example 2.

FIG. 4 A structure of a plasmid for preparing an adeno-associated virus vector expressing mVChR1-ClChR1-3TM in Example 3.

FIG. 5 A graph showing that mVChR1-ClChR1-3TM has higher ion permeability than mVChR1 in Example 3.

FIG. 6 Fluorescence micrographs showing that switCh2 has higher localization in a cell membrane than switCh in Example 4.

FIG. 7 A graph showing that switCh2-mut1 obtained by substituting glutamic acid at position 161 in switCh2 by threonine has higher ion permeability than switCh2 in Example 5.

MODE FOR CARRYING OUT THE INVENTION

A modified channel rhodopsin of the present invention is based on the modified channel rhodopsin reported by the present inventors in Patent Document 1. The modified channel rhodopsin is configured such that the expression efficiency on a cell membrane is improved by substituting an N-terminal region of a *Volvox carteri*-derived channel rhodopsin by an N-terminal region of a *Chlamydomonas reinhardtii*-derived channel rhodopsin-1 (which is a region involved in cell membrane-localized expression and includes no transmembrane domain), and specific examples thereof include a polypeptide composed of the amino acid sequence represented by SEQ ID NO: 1 (a polypeptide composed of the amino acid sequence represented by SEQ ID NO: 10 in Patent Document 1). The matters described in Patent Document 1 are treated as matters described in the present description.

The modified channel rhodopsin of the present invention is one obtained by substituting a C-terminal region of the modified channel rhodopsin reported by the present inventors in Patent Document 1 by a C-terminal region of a *Chlamydomonas reinhardtii*-derived channel rhodopsin-2 or a C-terminal region of a *Tetraselmis striata*-derived channel rhodopsin.

The modified channel rhodopsin of the present invention obtained by substituting a C-terminal region of the modified channel rhodopsin reported by the present inventors in Patent Document 1 by a C-terminal region of a *Chlamydomonas reinhardtii*-derived channel rhodopsin-2 is specifically one obtained by adding a C-terminal region of the *Chlamydomonas reinhardtii*-derived channel rhodopsin-2 containing at least amino acids at positions 270 to 315 in the amino acid sequence represented by SEQ ID NO: 2 to the C-terminus of a polypeptide containing at least amino acids at positions 1 to 307 in the amino acid sequence represented by SEQ ID NO: 1.

The modified channel rhodopsin of the present invention obtained by substituting a C-terminal region of the modified channel rhodopsin reported by the present inventors in Patent Document 1 by a C-terminal region of a *Tetraselmis striata*-derived channel rhodopsin is specifically one obtained by adding a C-terminal region of the *Tetraselmis striata*-derived channel rhodopsin containing at least amino acids at positions 252 to 292 in the amino acid sequence represented by SEQ ID NO: 3 to the C-terminus of a polypeptide containing at least amino acids at positions 1 to 307 in the amino acid sequence represented by SEQ ID NO: 1.

Here, in order for the modified channel rhodopsin of the present invention to have a property of opening an ion channel by irradiation with light in a wide wavelength range of visible light at, for example, 450 to 600 nm, and closing the ion channel by irradiation with light at a shorter wavelength than the wavelength at which the ion channel is opened such as 400 nm, it is preferred that an amino acid (cysteine) at position 166 in the amino acid sequence represented by SEQ ID NO: 1 is substituted by alanine. Further, an amino acid (aspartic acid) at position 194 in the amino acid sequence represented by SEQ ID NO: 1 may be substituted by cysteine, or an amino acid (histidine) at position 229 therein may be substituted by asparagine. In addition, it may have another site-specific mutation.

As a specific example of the modified channel rhodopsin of the present invention obtained by adding a C-terminal region of a *Chlamydomonas reinhardtii*-derived channel rhodopsin-2 containing at least amino acids at positions 270 to 315 in the amino acid sequence represented by SEQ ID NO: 2 to the C-terminus of a polypeptide which contains at least amino acids at positions 1 to 307 in the amino acid sequence represented by SEQ ID NO: 1 and is obtained by substituting an amino acid at position 166 by alanine, an amino acid at position 194 by cysteine, and an amino acid at position 229 by asparagine, a polypeptide composed of the amino acid sequence represented by SEQ ID NO: 4 is exemplified.

As a specific example of the modified channel rhodopsin of the present invention obtained by adding a C-terminal region of a *Tetraselmis striata*-derived channel rhodopsin containing at least amino acids at positions 252 to 292 in the amino acid sequence represented by SEQ ID NO: 3 to the C-terminus of a polypeptide which contains at least amino acids at positions 1 to 307 in the amino acid sequence represented by SEQ ID NO: 1 and is obtained by substituting an amino acid at position 166 by alanine, an amino acid at position 194 by cysteine, and an amino acid at position 229 by asparagine, a polypeptide composed of the amino acid sequence represented by SEQ ID NO: 5 is exemplified.

Further, amino acids at positions 142 to 169 in the amino acid sequence represented by SEQ ID NO: 1 may be substituted by amino acids at positions 143 to 170 in the amino acid sequence of a *Chlamydomonas reinhardtii*-derived channel rhodopsin-1 represented by SEQ ID NO: 6. This substitution means substitution of the third transmembrane domain of seven transmembrane domains included in the modified channel rhodopsin reported by the present inventors in Patent Document 1 (that is, seven transmembrane domains included in a *Volvox carteri*-derived channel rhodopsin) by the third transmembrane domain of seven transmembrane domains included in the *Chlamydomonas reinhardtii*-derived channel rhodopsin-1, and by this substitution, the ion permeability can be enhanced.

In that case, for example, in order to have a property of opening an ion channel by irradiation with light in a wide wavelength range of visible light at, for example, 450 to 600 nm, and closing the ion channel by irradiation with light at a shorter wavelength than the wavelength at which the ion channel is opened such as 400 nm, it is preferred that an amino acid (cysteine) at position 167 (at position 166 after substitution of amino acids at positions 142 to 169 in the amino acid sequence represented by SEQ ID NO: 1) in the amino acid sequence represented by SEQ ID NO: 6 is substituted by alanine. Further, an amino acid (aspartic acid) at position 194 in the amino acid sequence represented by SEQ ID NO: 1 may be substituted by cysteine, or an amino acid (histidine) at position 229 therein may be substituted by asparagine. In addition, it may have another site-specific mutation.

Further, the ion permeability can be enhanced by substituting an amino acid (glutamic acid) at position 162 (at position 161 after substitution of amino acids at positions 142 to 169 in the amino acid sequence represented by SEQ ID NO: 1) in the amino acid sequence represented by SEQ ID NO: 6 by threonine. In addition, an amino acid (leucine) at position 170 in the amino acid sequence represented by SEQ ID NO: 1 may be substituted by cysteine, or an amino acid (cysteine) at position 197 therein may be substituted by serine.

As a specific example of the modified channel rhodopsin of the present invention obtained by adding a C-terminal region of a *Chlamydomonas reinhardtii*-derived channel rhodopsin-2 containing at least amino acids at positions 270 to 315 in the amino acid sequence represented by SEQ ID NO: 2 to the C-terminus of a polypeptide which contains at least amino acids at positions 1 to 307 in the amino acid sequence represented by SEQ ID NO: 1 and is obtained by substituting amino acids at positions 142 to 169 by amino acids at positions 143 to 170 in the amino acid sequence of a *Chlamydomonas reinhardtii*-derived channel rhodopsin-1 represented by SEQ ID NO: 6, and further substituting an amino acid at position 166 by alanine, an amino acid at position 194 by cysteine, and an amino acid at position 229 by asparagine, a polypeptide composed of the amino acid sequence represented by SEQ ID NO: 7 is exemplified.

As a specific example of the modified channel rhodopsin of the present invention obtained by adding a C-terminal region of a *Tetraselmis striata*-derived channel rhodopsin containing at least amino acids at positions 252 to 292 in the amino acid sequence represented by SEQ ID NO: 3 to the C-terminus of a polypeptide which contains at least amino acids at positions 1 to 307 in the amino acid sequence represented by SEQ ID NO: 1 and is obtained by substituting amino acids at positions 142 to 169 by amino acids at positions 143 to 170 in the amino acid sequence of a *Chlamydomonas reinhardtii*-derived channel rhodopsin-1 represented by SEQ ID NO: 6, and further substituting an amino acid at position 166 by alanine, an amino acid at position 194 by cysteine, and an amino acid at position 229 by asparagine, a polypeptide composed of the amino acid sequence represented by SEQ ID NO: 8 is exemplified.

As a specific example of the modified channel rhodopsin of the present invention obtained by adding a C-terminal region of a *Chlamydomonas reinhardtii*-derived channel rhodopsin-2 containing at least amino acids at positions 270 to 315 in the amino acid sequence represented by SEQ ID NO: 2 to the C-terminus of a polypeptide which contains at least amino acids at positions 1 to 307 in the amino acid sequence represented by SEQ ID NO: 1 and is obtained by substituting amino acids at positions 142 to 169 by amino acids at positions 143 to 170 in the amino acid sequence of a *Chlamydomonas reinhardtii*-derived channel rhodopsin-1 represented by SEQ ID NO: 6, and further substituting an amino acid at position 161 by threonine, an amino acid at position 166 by alanine, an amino acid at position 194 by cysteine, and an amino acid at position 229 by asparagine, a polypeptide composed of the amino acid sequence represented by SEQ ID NO: 9 is exemplified.

As a specific example of the modified channel rhodopsin of the present invention obtained by substituting the third transmembrane domain of seven transmembrane domains included in the modified channel rhodopsin reported by the present inventors in Patent Document 1 by the third transmembrane domain of seven transmembrane domains included in a *Chlamydomonas reinhardtii*-derived channel rhodopsin-1, a polypeptide composed of the amino acid sequence represented by SEQ ID NO: 10 is exemplified.

The modified channel rhodopsin of the present invention includes a polypeptide that includes deletion, substitution, addition, or insertion of one or a plurality of amino acids in the amino acid sequence represented by each of SEQ ID NOS: 4, 5, and 7 to 10, and that has a biological activity equivalent to that of the polypeptide composed of the amino acid sequence represented by each of SEQ ID NOS: 4, 5, and 7 to 10. Further, it includes a polypeptide that is composed of an amino acid sequence having at least 90% sequence identity to the amino acid sequence represented by each of SEQ ID NOS: 4, 5, and 7 to 10, and that has a biological activity equivalent to that of the polypeptide composed of the amino acid sequence represented by each of SEQ ID NOS: 4, 5, and 7 to 10. Here, the "a plurality of" is an integer of 50 or less, preferably an integer of 30 or less, more preferably an integer of 10 or less, and, for example, 2 to 9, 2 to 7, or 2 to 5. The sequence identity to the amino acid sequence represented by each of SEQ ID NOS: 4, 5, and 7 to 10 is preferably at least 95%, more preferably at least 96%, further more preferably at least 97%, still further more preferably at least 98%, and most preferably at least 99%. Note that the % of the identity refers to a value calculated using a software for calculating the identity between a plurality of (two) amino acid sequences (e.g., FASTA, DANASYS, BLAST, etc.) with default settings. The "equivalent biological activity" means that, for example, the intensity of a biological activity such as light sensitivity or channel function is substantially the same. Further, this term may include a case of having a biological activity of substantially the same quality, and the biological activity of "the same quality" in that case means that a property such as a light sensitive wavelength or ion permeability is the same.

The modified channel rhodopsin of the present invention can be produced by a genetic engineering technique. Specifically, first, a polynucleotide encoding the modified channel rhodopsin of the present invention (hereinafter, referred to as "the modified channel rhodopsin gene of the present invention") is prepared. The modified channel rhodopsin gene of the present invention can be prepared by a method known to those skilled in the art. Specifically, for example, the gene can be prepared by chemical synthesis based on the sequence information of each of a polynucleotide encoding the modified channel rhodopsin reported by the present inventors in Patent Document 1, a polynucleotide encoding a *Chlamydomonas reinhardtii*-derived channel rhodopsin-2, a polynucleotide encoding a *Tetraselmis striata*-derived channel rhodopsin, and a polynucleotide encoding a *Chlamydomonas reinhardtii*-derived channel rhodopsin-1. Further, the gene can also be prepared by amplifying a desired region of each of the polynucleotides using PCR primers that amplify the desired region of each of the polynucleotides based on the sequence information of each of the polynucleotides, and linking these regions. Subsequently, the modified channel rhodopsin gene of the present invention functionally linked to a promoter is integrated into an expression vector that can maintain replication in a host bacterial cell, can stably express the encoded polypeptide, and can stably maintain the gene, a host is transformed using the obtained recombinant expression vector, and the modified channel rhodopsin of the present invention can be produced in the host. For the recombination technique, Proc. Natl. Acad. Sci. USA., 1984 81: 5662, or Molecular Cloning: A Laboratory Manual (1989) Second Edition, Cold Spring Harbor Laboratory Press, or the like can be referred to. As the expression vector, *Escherichia coli*-derived plasmids (e.g., pET28, pGEX4T, pUC118, pUC119, pUC18, pUC19, and other plasmid DNAs), *Bacillus subtilis*-derived plasmids (e.g., pUB110, pTP5, and other plasmid DNAs), yeast-derived plasmids (e.g., YEp13, YEp24, YCp50, and other plasmid DNAs), λ phages (Agt11 and AZAP), plasmids for use in mammals (pCMV and pSV40), virus vectors (e.g., animal virus vectors such as adenovirus vectors, adeno-associated virus vectors, retrovirus vectors, lentivirus vectors, or vaccinia virus vectors, and insect virus vectors such as baculovirus vectors), vectors for use in plants (e.g., binary vector pBI series), cosmid vectors, and the like can be used. Here, the "functionally linked" refers to a functional bond between a promoter sequence and a target polynucleotide sequence such that the promoter sequence can start transcription of the target polynucleotide sequence. The promoter is not particularly limited, and a suitable promoter may only be selected according to the host, and a known constitutive promoter or an inducible promoter can be used, but a constitutive promoter is preferably used. Specific examples thereof include CMV promoter, SV40 promoter, CAG promoter, synapsin promoter, rhodopsin promoter, CaMV promoter, glycolytic enzyme promoter, lac promoter, trp promoter, tac promoter, GAPDH promoter, GAL1 promoter, PH05 promoter, PGK promoter, and thy1 promoter. The insertion of the modified channel rhodopsin gene of the present invention into an expression vector is carried out, for example, by creating or linking a restriction enzyme site flanking the modified channel rhodopsin gene of the present invention, and inserting the resultant into a restriction enzyme site or a multicloning site of a suitable vector DNA. The expression vector may include, in addition to a promoter and the modified channel rhodopsin gene of the present invention, an enhancer and other cis elements, a splicing signal, a polyA addition signal, a selection marker (a drug resistance gene marker such as an ampicillin resistance marker or a tetracycline resistance marker, an auxotrophic complementary gene marker such as LEU1, TRP1, or URA3, a dominant selection marker such as APH, DHFR, or TK, etc.), a ribosome binding site (RBS), or the like as needed. The transformation of the host can be carried out using a protoplast method, a spheroplast method, a competent cell method, a virus method, a calcium phosphate method, a lipofection method, a microinjection method, a gene bombardment method, an *agrobacterium* method, electroporation, or the like. The thus obtained transformant is cultured under appropriate conditions using a medium containing an assimilable carbon source, a nitrogen source, a metal salt, a vitamin, or the like. The culture of the transformant is usually carried out under aerobic conditions such as shake culture or aerated and agitated culture at 25 to 37° C. for 3 to 6 hours. The pH is kept around neutral during the period of culture. The pH is adjusted using an inorganic or organic acid, an alkaline solution, or the like. During the culture, an antibiotic such as ampicillin or tetracycline may be added to the medium according to the selection marker inserted into the recombinant expression vector as needed. Further, the host used for the transformation is not particularly limited as long as it can express the modified channel rhodopsin of the present invention, and examples thereof include bacteria (*Escherichia coli* and *Bacillus subtilis*), yeasts (*Saccharomyces cerevisiae*, etc.), animal cells (COS cells, Chinese hamster ovary (CHO) cells, 3T3 cells, BHK cells, HEK293 cells, etc.), and insect cells. The modified channel rhodopsin of the present invention can be obtained in the form of retaining its activity by fractionation or purification using a common method from a culture (a culture supernatant, cultured cells, cultured bacterial cells, a homogenate of cells or bacterial cells, or the like) obtained by culturing the transformant, followed by ultrafiltration concentration, lyophilization, spray drying, crystallization, or the like. Alternatively, the modified channel rhodopsin of the present invention may be provided in the form of cells expressing the modified channel rhodopsin of the present invention without performing isolation or purification. In that case, the host cells used for the transformation are host cells suitable for subsequent use, for example, visual cells, preferably human visual cells. Further, when the modified channel rhodopsin of the present invention is used for a medical application, it may be provided in the form of an expression vector for the modified channel rhodopsin of the present invention. In that case, it is preferred to use an expression vector having excellent introduction efficiency into cells, replication maintenance in cells, stability, expression efficiency, and the like. Examples of such a vector can include virus vectors such as an adeno-associated virus vector, a retrovirus vector, and a lentivirus vector, (autonomously replicable) plasmids, and transposons. The plasmid for preparing an expression vector for the modified channel rhodopsin of the present invention can be prepared according to the method described, for example, in Tomita H et al., Invest Ophthalmol Vis Sci. 2007 August; 48 (8): 3821-6, or Sugano E et al., Invest Ophthalmol Vis Sci. 2005 September; 46(9): 3341-8.

Here, examples of the modified channel rhodopsin gene of the present invention include a polynucleotide composed of the nucleotide sequence represented by SEQ ID NO: 11 (encoding a polypeptide composed of the amino acid sequence represented by SEQ ID NO: 4), a polynucleotide composed of the nucleotide sequence represented by SEQ ID NO: 12 (encoding a polypeptide composed of the amino acid sequence represented by SEQ ID NO: 5), a polynucleotide composed of the nucleotide sequence represented by SEQ ID NO: 13 (encoding a polypeptide composed of the amino acid sequence represented by SEQ ID NO: 7), a polynucleotide composed of the nucleotide sequence represented by SEQ ID NO: 14 (encoding a polypeptide composed of the amino acid sequence represented by SEQ ID NO: 8), a polynucleotide composed of the nucleotide sequence represented by SEQ ID NO: 15 (encoding a polypeptide composed of the amino acid sequence represented by SEQ ID NO: 9), and a polynucleotide composed of the nucleotide sequence represented by SEQ ID NO: 16 (encoding a polypeptide composed of the amino acid sequence represented by SEQ ID NO: 10). However, the modified channel rhodopsin gene of the present invention is not limited to these polynucleotides, and includes a polynucleotide that hybridizes to a complementary strand of each of these polynucleotides under stringent conditions and encodes a polypeptide having a biological activity equivalent to that of the polypeptide composed of the amino acid sequence represented by each of SEQ ID NOS: 4, 5, and 7 to 10. Further, the gene includes a polynucleotide that has at least 90%, preferably at least 95%, more preferably at least 961, further more preferably at least 97%, still further more preferably at least 98%, and most preferably at least 99% sequence identity to the nucleotide sequence represented by each of SEQ ID NOS: 11 to 16 and that encodes a polypeptide having a biological activity equivalent to that of the polypeptide composed of the amino acid sequence represented by each of SEQ ID NOS: 4, 5, and 7 to 10. Here, the "hybridization under stringent conditions" include, for example, hybridization in 3 to 4×SSC (150 mM sodium chloride, 15 mM sodium citrate, pH 7.2) and 0.1 to 0.5% SDS at 30 to 50° C. for 1 to 24 hours, preferably hybridization in 3.4×SSC and 0.3% SDS at 40 to 45° C. for 1 to 24 hours, and subsequent washing. As washing conditions, for example, conditions such as continuous washing with a solution containing 2×SSC and 0.1% SDS, a 1×SSC solution, and a 0.2×SSC solution at room temperature are exemplified. However, the combination of the above conditions is exemplary, and those skilled in the art can achieve the same stringency as described above by properly combining the above or other factors determining hybridization stringency (for example, the concentration, length, and GC content of a hybridization probe, the reaction time of hybridization, etc.).

The modified channel rhodopsin of the present invention maintains the property of the modified channel rhodopsin reported by the present inventors in Patent Document 1 that the expression efficiency on a cell membrane is high, and moreover has a property of opening an ion channel by irradiation with light in a wide wavelength range of visible light and closing the ion channel by irradiation with light at a shorter wavelength than the wavelength at which the ion channel is opened, or a property of having high ion permeability. Therefore, the modified channel rhodopsin of the present invention and an expression vector including a polynucleotide encoding the modified channel rhodopsin are useful for treating a subject suffering from damage to the outer retinal layers. Here, the "damage to the outer retinal layers" refers to any disease in which cells other than visual cells remain normal or retain some of their functions although visual dysfunction or visual function impairment occurs as by the degeneration or loss of visual cells present in the outer retinal layers. As such a disease, retinitis pigmentosa, age-related macular degeneration, retinal detachment, and the like can be exemplified. The "subject" means a subject with visual loss or a subject at risk for visual loss due to damage to the outer retinal layers. The subject is not limited to a human and may be any other mammal. Examples of such other mammal include mice, rats, monkeys, rabbits, dogs, cats, cattle, and horses. The "treatment of a subject suffering from damage to the outer retinal layers" means recovery of visual function as compared with before administration of the pharmaceutical of the present invention in a subject with visual loss or at risk for visual loss due to damage to the outer retinal layers.

The pharmaceutical composition of the present invention contains the modified channel rhodopsin of the present invention or the expression vector including a polynucleotide encoding the modified channel rhodopsin as an active ingredient, and is formulated as a pharmaceutical for treating a subject suffering from damage to the outer retinal layers. The effective dose thereof is an amount that can have a therapeutic effect on a given symptom or usage, and is properly determined by those skilled in the art based on implementation of a test using an animal or a clinical test, however, the age, body weight, and sex of the subject being an administration target, the condition or severity of the disease, the administration method, and the like are considered. In the case of a virus, the viral dose is, for example, $10^{12}$ to $10^1$ capsids/ml (e.g., about $10^{13}$ capsids/ml). In the formulation as a pharmaceutical, the active ingredient may be formulated together with one or more pharmaceutically acceptable carriers. Examples of the pharmaceutically acceptable carrier include various buffer solutions, for example, saline and buffer solutions of phosphates, acetates, and the like. The pharmaceutical may contain another therapeutic ingredient. Examples of the another therapeutic ingredient include agents known as therapeutic agents for retinitis pigmentosa, age-related macular degeneration, retinal detachment, or the like. The pharmaceutical can be formulated, for example, into an injection for local administration, an eye drop, an eye wash, or the like. An injectable preparation can be provided, for example, as an ample or in a unit dosage form in a container for multiple administrations, by adding a preservative. Further, the pharmaceutical may be in the form of a lyophilized preparation to be reconstituted before use with a suitable vehicle, for example, pyrogen-free sterile water or the like. The pharmaceutical is preferably administered by direct injection into the affected area of a subject, that is, the retina, or direct contact to the vitreous body.

EXAMPLES

Hereinafter, the present invention will be described in detail by way of Examples, however, the present invention should not be construed as being limited to the following description.

Example 1: Modified Channel Rhodopsin of Present Invention Composed of Amino Acid Sequence Represented by SEQ ID NO: 4 (Abbreviation: neomVChR1)

(Acquisition of Cells Expressing neomVChR1)

The cells were obtained according to the method described in Patent Document 1. A polynucleotide, in which a region of a polynucleotide encoding amino acids at positions 1 to 307 (provided that an amino acid at position 166 was substituted by alanine, an amino acid at position 194 was substituted by cysteine, and an amino acid at position 229 was substituted by asparagine) in the modified channel rhodopsin composed of the amino acid sequence represented by SEQ ID NO: 1 described in Patent Document 1 and a region of a polynucleotide encoding amino acids at positions 270 to 315 in the amino acid sequence represented by SEQ ID NO: 2 of a *Chlamydomonas reinhardtii*-derived channel rhodopsin-2 were linked, and a restriction enzyme sequence was added to the 5' end and the 3' end, was chemically synthesized and inserted into a multicloning site of a plasmid for preparing an adeno-associated virus vector. The structure of the thus prepared plasmid for preparing an adeno-associated virus vector expressing neomVChR1 is shown in FIG. 1. In the plasmid, a fluorescent protein gene (venus) is located in a 3' region of the multicloning site, and the target gene is expressed in the form of a fusion protein with venus attached to a C-terminal region, and therefore, cells expressing neomVChR1 were fractionated using a cell sorter (SH-800, Sony) using venus as an index. Note that as the cells, human embryonic kidney (HEK) 293 cells were used and cultured in DMEM medium containing 10% FBS at 37° C. and 5% $CO_2$. The plasmid for preparing an adeno-associated virus vector expressing neomVChR1 was made linear by cleavage with a restriction enzyme together with two types of plasmids (pAAV-RC and pHelper), and thereafter introduced into cells by an electroporation method (CUY21Pro-vitro system, Nepa Gene).

(Measurement of Light-Induced Current by Patch Clamp Method)

With respect to the cells expressing neomVChR1, after confirming the expression of venus under a microscope, measurement was performed using a patch clamp system (EPC-10, HEKA). As a solution outside the cells, a solution composed of 138 mM NaCl, 3 mM KCl, 10 mM HEPES, 4 mM NaOH, 1 mM CaCl$_2$, and 2 mM MgCl$_2$ and adjusted to pH 7.4 with 1 N HCl was used. As a solution in the electrode, a solution composed of 130 mM CsCl, 1.1 mM EGTA, 2 mM MgCl$_2$, 0.1 mM CaCl$_2$, 10 mM NaCl, 10 mM HEPES, and 2 mM Na$_2$ATP and adjusted to pH 7.2 with 1 N CsOH was used. Light irradiation was performed for 1 second, and the intensity was set to 1 µW/mm$^2$. The wavelength was set to each of 400, 450, 500, 550, and 600 nm. The results are shown in FIG. 2. As apparent from FIG. 2, it was found that neomVChR1 has a property of opening an ion channel by irradiation with light in a wide wavelength range of visible light at 450 to 600 nm, and closing the ion channel by irradiation with light at 400 nm which is shorter than the wavelength at which the ion channel is opened.

Example 2: Modified Channel Rhodopsin of Present Invention Composed of Amino Acid Sequence Represented by SEQ ID NO: 8 (Abbreviation: switCh)

Cells expressing switCh were fractionated in the same manner as in Example 1 except that a polynucleotide, in which a region of a polynucleotide encoding amino acids at positions 1 to 141 in the modified channel rhodopsin composed of the amino acid sequence represented by SEQ ID NO: 1 described in Patent Document 1, a region of a polynucleotide encoding amino acids at positions 143 to 170 (provided that an amino acid at position 167 was substituted by alanine) in the amino acid sequence represented by SEQ ID NO: 6 of a *Chlamydomonas reinhardtii*-derived channel rhodopsin-1, a region of a polynucleotide encoding amino acids at positions 170 to 307 (provided that an amino acid at position 194 was substituted by cysteine, and an amino acid at position 229 was substituted by asparagine) in the amino acid sequence represented by SEQ ID NO: 1, and a region of a polynucleotide encoding amino acids at positions 252 to 292 in the amino acid sequence represented by SEQ ID NO: 3 of a *Tetraselmis striata*-derived channel rhodopsin were linked, and a restriction enzyme sequence was added to the 5' end and the 3' end, was chemically synthesized and inserted into a multicloning site of a plasmid for preparing an adeno-associated virus vector. With respect to the thus obtained cells expressing switCh, measurement of a light-induced current by a patch clamp method was performed in the same manner as in Example 1. The results are shown in FIG. 3. As apparent from FIG. 3, it was found that switCh has higher ion permeability than neomVChR1.

Example 3: Modified Channel Rhodopsin of Present Invention Composed of Amino Acid Sequence Represented by SEQ ID NO: 10 (Abbreviation: mVChR1-ClChR1-3TM)

(Acquisition of Cells Expressing mVChR1-ClChR1-3TM)

Cells expressing mVChR1-ClChR1-3TM were fractionated in the same manner as in Example 1 except that a polynucleotide, in which a region of a polynucleotide encoding amino acids at positions 1 to 141 in the modified channel rhodopsin composed of the amino acid sequence represented by SEQ ID NO: 1 described in Patent Document 1, a region of a polynucleotide encoding amino acids at positions 143 to 170 in the amino acid sequence represented by SEQ ID NO: 6 of a *Chlamydomonas reinhardtii*-derived channel rhodopsin-1, and a region of a polynucleotide encoding amino acids at positions 170 to 343 in the amino acid sequence represented by SEQ ID NO: 1 were linked, and a restriction enzyme sequence was added to the 5' end and the 3' end, was chemically synthesized and inserted into a multicloning site of a plasmid for preparing an adeno-associated virus vector. The structure of the plasmid for preparing an adeno-associated virus vector expressing mVChR1-ClChR1-3TM is shown in FIG. 4.

(Measurement of Light-Induced Current by Patch Clamp Method)

With respect to the cells expressing mVChR1-ClChR1-3TM, measurement of a light-induced current by a patch clamp method was performed in the same manner as in Example 1. The results are shown in FIG. 5. In FIG. 5, the measurement results with respect to the modified channel rhodopsin (abbreviation: mVChR1) composed of the amino acid sequence represented by SEQ ID NO: 1 described in Patent Document 1 obtained in the same manner as for the cells expressing mVChR1-ClChR1-3TM are also shown. As apparent from FIG. 5, mVChR1-ClChR1-3TM has higher ion permeability than mVChR1, and therefore, it was found that the ion permeability can be enhanced by substituting the third transmembrane domain of seven transmembrane domains included in mVChR1 (that is, seven transmembrane domains included in a *Volvox carteri*-derived channel rhodopsin) by the third transmembrane domain of seven transmembrane domains included in a *Chlamydomonas reinhardtii*-derived channel rhodopsin-1.

Example 4: Modified Channel Rhodopsin of Present Invention Composed of Amino Acid Sequence Represented by SEQ ID NO: 7 (Abbreviation: switCh2)

Cells expressing switCh2 were fractionated in the same manner as in Example 1 except that a polynucleotide, in which a region of a polynucleotide encoding amino acids at positions 1 to 141 in the modified channel rhodopsin composed of the amino acid sequence represented by SEQ ID NO: 1 described in Patent Document 1, a region of a polynucleotide encoding amino acids at positions 143 to 170 (provided that an amino acid at position 167 was substituted by alanine) in the amino acid sequence represented by SEQ ID NO: 6 of a *Chlamydomonas reinhardtii*-derived channel rhodopsin-1, a region of a polynucleotide encoding amino acids at positions 170 to 307 (provided that an amino acid at position 194 was substituted by cysteine, and an amino acid at position 229 was substituted by asparagine) in the amino acid sequence represented by SEQ ID NO: 1, and a region of a polynucleotide encoding amino acids at positions 270 to 315 in the amino acid sequence represented by SEQ ID NO: 2 of a *Chlamydomonas reinhardtii*-derived channel rhodopsin-2 were linked, and a restriction enzyme sequence was added to the 5' end and the 3' end, was chemically synthesized and inserted into a multicloning site of a plasmid for preparing an adeno-associated virus vector. A fluorescence micrograph of the thus obtained cells expressing switCh2 is shown in FIG. 6. In FIG. 6, a fluorescence micrograph of the cells expressing switCh obtained in Example 2 is also shown. As apparent from FIG. 6, it was found that switCh2 has higher localization in a cell membrane than switCh. From the results, it was considered that as the C-terminal region of the modified channel rhodopsin of the present invention, the C-terminal region of a *Chlamydomonas reinhardtii*-derived channel rhodopsin-2 is more advantageous than the C-terminal region of a *Tetraselmis striata*-derived channel rhodopsin from the viewpoint that the localization in a cell membrane is higher.

Example 5: Examination of Ion Permeability of Mutants of Modified Channel Rhodopsin of Present Invention Composed of Amino Acid Sequence Represented by SEQ ID NO: 7 (Abbreviation: switCh2)

(Examination Method)

Cells expressing the following 7 types of mutants of switCh2 were obtained in the same manner as the cells expressing switCh2 in Example 4, and a light-induced current by a patch clamp method was measured in the same manner as in Example 1.

switCh2-mut1: a mutant in which glutamic acid at position 161 in switCh2 was substituted by threonine (E161T)

switCh2-mut2: a mutant in which leucine at position 170 in switCh2 was substituted by cysteine (L170C)

switCh2-mut3: a mutant in which cysteine at position 197 in switCh2 was substituted by serine (C197S)

switCh2-mut4: a mutant in which glutamic acid at position 161 in switCh2 was substituted by threonine and leucine at position 170 therein was substituted by cysteine (E161T+L170C)

switCh2-mut5: a mutant in which glutamic acid at position 161 in switCh2 was substituted by threonine and cysteine at position 197 therein was substituted by serine (E161T+C197S)

switCh2-mut6: a mutant in which leucine at position 170 in switCh2 was substituted by cysteine and cysteine at position 197 therein was substituted by serine (L170C+C197S)

switCh2-mut7: a mutant in which glutamic acid at position 161 in switCh2 was substituted by threonine, leucine at position 170 therein was substituted by cysteine, and cysteine at position 197 therein was substituted by serine (E161T+L170C+C197S)

(Results of Examination)

It was found that the ion permeability is improved by substituting glutamic acid at position 161 in switCh2 by threonine. The measurement results of switCh and switCh2-mut1 (composed of the amino acid sequence represented by SEQ ID NO:9) are shown in FIG. 7.

INDUSTRIAL APPLICABILITY

The present invention has industrial applicability in that it can provide a modified channel rhodopsin capable of opening and closing an ion channel by irradiation with light at different wavelengths, and/or having high ion permeability (photoreactivity).

---

The invention claimed is:

1. A modified channel rhodopsin, which is any one of the following (a) to (1):
   (a) a polypeptide composed of the amino acid sequence represented by SEQ ID NO: 4;
   (b) a polypeptide that is composed of an amino acid sequence having at least 95% sequence identity to the amino acid sequence represented by SEQ ID NO: 4, and that has a biological activity equivalent to that of the polypeptide (a);
   (c) a polypeptide composed of the amino acid sequence represented by SEQ ID NO: 5;
   (d) a polypeptide that is composed of an amino acid sequence having at least 95% sequence identity to the amino acid sequence represented by SEQ ID NO: 5, and that has a biological activity equivalent to that of the polypeptide (c);
   (e) a polypeptide composed of the amino acid sequence represented by SEQ ID NO: 7;
   (f) a polypeptide that is composed of an amino acid sequence having at least 90% sequence identity to the amino acid sequence represented by SEQ ID NO: 7, and that has a biological activity equivalent to that of the polypeptide (e);
   (g) a polypeptide composed of the amino acid sequence represented by SEQ ID NO: 8;
   (h) a polypeptide that is composed of an amino acid sequence having at least 90% sequence identity to the amino acid sequence represented by SEQ ID NO: 8, and that has a biological activity equivalent to that of the polypeptide (g);
   (i) a polypeptide composed of the amino acid sequence represented by SEQ ID NO: 9;
   (j) a polypeptide that is composed of an amino acid sequence having at least 90% sequence identity to the amino acid sequence represented by SEQ ID NO: 9, and that has a biological activity equivalent to that of the polypeptide (i);

(k) a polypeptide composed of the amino acid sequence represented by SEQ ID NO: 10; and (l) a polypeptide that is composed of an amino acid sequence having at least 98% sequence identity to the amino acid sequence represented by SEQ ID NO: 10, and that has a biological activity equivalent to that of the polypeptide (k).

2. A polynucleotide encoding a modified channel rhodopsin that is one of the following polypeptides (a) to (l):

(a) a polypeptide composed of the amino acid sequence represented by SEQ ID NO: 4;

(b) a polypeptide that is composed of an amino acid sequence having at least 95% sequence identity to the amino acid sequence represented by SEQ ID NO: 4, and that has a biological activity equivalent to that of the polypeptide (a);

(c) a polypeptide composed of the amino acid sequence represented by SEQ ID NO: 5;

(d) a polypeptide that is composed of an amino acid sequence having at least 95% sequence identity to the amino acid sequence represented by SEQ ID NO: 5, and that has a biological activity equivalent to that of the polypeptide (c);

(e) a polypeptide composed of the amino acid sequence represented by SEQ ID NO: 7;

(f) a polypeptide that is composed of an amino acid sequence having at least 90% sequence identity to the amino acid sequence represented by SEQ ID NO: 7, and that has a biological activity equivalent to that of the polypeptide (e);

(g) a polypeptide composed of the amino acid sequence represented by SEQ ID NO: 8;

(h) a polypeptide that is composed of an amino acid sequence having at least 90% sequence identity to the amino acid sequence represented by SEQ ID NO: 8, and that has a biological activity equivalent to that of the polypeptide (g);

(i) a polypeptide composed of the amino acid sequence represented by SEQ ID NO: 9;

(j) a polypeptide that is composed of an amino acid sequence having at least 90% sequence identity to the amino acid sequence represented by SEQ ID NO: 9, and that has a biological activity equivalent to that of the polypeptide (i);

(k) a polypeptide composed of the amino acid sequence represented by SEQ ID NO: 10; and (l) a polypeptide that is composed of an amino acid sequence having at least 98% sequence identity to the amino acid sequence represented by SEQ ID NO: 10, and that has a biological activity equivalent to that of the polypeptide (k).

3. An expression vector comprising the polynucleotide according to claim 2 functionally linked to a promoter.

4. An isolated cell produced by transforming a cell with the expression vector according to claim 3.

5. The isolated cell according to claim 4, wherein the cell is a retinal cell.

6. A method for treating a subject suffering from damage to the outer retinal layers, comprising administering to said subject an effective amount of the modified channel rhodopsin according to claim 1, the polynucleotide according to claim 2, or the expression vector according to claim 3.

7. The method according to claim 6, wherein the damage to the outer retinal layers is retinitis pigmentosa, age-related macular degeneration, or retinal detachment.

8. A pharmaceutical composition for treating damage to the outer retinal layers, comprising either the modified channel rhodopsin according to claim 1 or the expression vector according to claim 3 as an active ingredient.

* * * * *